United States Patent
Endo et al.

(10) Patent No.: US 10,670,304 B2
(45) Date of Patent: Jun. 2, 2020

(54) HEAT IMPLEMENT AND METHOD FOR MANUFACTURING SAME

(71) Applicant: Kao Corporation, Tokyo (JP)

(72) Inventors: Youichi Endo, Utsunomiya (JP); Hideo Kobayashi, Mooka (JP); Ryosuke Manabe, Oyama (JP)

(73) Assignee: Kao Corporation, Tokyo (JP)

( * ) Notice: Subject to any disclaimer, the term of this patent is extended or adjusted under 35 U.S.C. 154(b) by 130 days.

(21) Appl. No.: 15/740,633

(22) PCT Filed: Jul. 7, 2016

(86) PCT No.: PCT/JP2016/070060
§ 371 (c)(1),
(2) Date: Dec. 28, 2017

(87) PCT Pub. No.: WO2017/014053
PCT Pub. Date: Jan. 26, 2017

(65) Prior Publication Data
US 2018/0195765 A1 Jul. 12, 2018

(30) Foreign Application Priority Data
Jul. 21, 2015 (JP) .................................. 2015-143584

(51) Int. Cl.
*F24V 30/00* (2018.01)
*A61F 7/03* (2006.01)
(52) U.S. Cl.
CPC ................ *F24V 30/00* (2018.05); *A61F 7/03* (2013.01); *A61F 7/034* (2013.01)
(58) Field of Classification Search
CPC ....................................................... A61F 7/03
(Continued)

(56) References Cited

U.S. PATENT DOCUMENTS

| | | | |
|---|---|---|---|
| 6,629,964 | B1 | 10/2003 | Ono et al. |
| 2002/0151947 | A1* | 10/2002 | Usui ........................ A61F 7/03 607/111 |

(Continued)

FOREIGN PATENT DOCUMENTS

| | | |
|---|---|---|
| CN | 104010599 | 8/2014 |
| CN | 104334130 | 2/2015 |

(Continued)

OTHER PUBLICATIONS

Extended European Search Report dated Mar. 18, 2019 in European Patent Application No. 16827615.2, 9 pages.
(Continued)

*Primary Examiner* — Avinash A Savani
(74) *Attorney, Agent, or Firm* — Oblon, McClelland, Maier & Neustadt, L.L.P.

(57) ABSTRACT

An exothermic warmer (1) includes an exothermic element (11) that is covered with a first cover sheet (21) and a second cover sheet (22). The first cover sheet (21) is a sheet that is air permeable and does not substantially limit an oxidation reaction. A water-retaining material (12) is provided so as to be at least partially in contact with the exothermic element (11). The exothermic warmer (1) satisfies the following conditions (A) to (C): (A) the difference between the internal temperature of the exothermic element and the highest surface temperature of the exothermic warmer is 10° C. or less; (B) the highest skin temperature obtained when the exothermic warmer is applied to human skin is 38° C. or more and 42° C. or less; and (C) the ratio of the amount ($mg/cm^2 \cdot 10$ min) of steam generated in 10 minutes after the start of the oxidation reaction to the mass ($g/cm^2$) of the exothermic element takes a value of 50 or more and 250 or less.

44 Claims, 6 Drawing Sheets

(58) Field of Classification Search
USPC .............................. 126/236.01, 263.1; 122/21
See application file for complete search history.

(56) References Cited

U.S. PATENT DOCUMENTS

| | | |
|---|---|---|
| 2002/0161420 A1 | 10/2002 | Usui |
| 2005/0192653 A1 | 9/2005 | Tsunakawa et al. |
| 2006/0276863 A1 | 12/2006 | Kumamoto et al. |
| 2008/0234789 A1 | 9/2008 | Freeland et al. |
| 2009/0062890 A1* | 3/2009 | Ugajin .................. A61F 7/034 607/104 |
| 2010/0010598 A1* | 1/2010 | Igaki ...................... A61F 7/034 607/109 |
| 2010/0241089 A1* | 9/2010 | Uchiyama ............. A61F 7/034 604/291 |
| 2012/0022621 A1 | 1/2012 | Wong et al. |
| 2013/0125837 A1* | 5/2013 | Ueno ..................... A61F 7/034 122/21 |
| 2014/0345543 A1 | 11/2014 | Saita et al. |
| 2014/0373828 A1 | 12/2014 | Oka |
| 2015/0184891 A1 | 7/2015 | Oka et al. |

FOREIGN PATENT DOCUMENTS

| | | |
|---|---|---|
| EP | 1 147 752 A1 | 10/2001 |
| EP | 1 623 689 A1 | 2/2006 |
| JP | 9-75388 A | 3/1997 |
| JP | 11-342147 A | 12/1999 |
| JP | 2001-187727 A | 7/2001 |
| JP | 2002-78728 A | 3/2002 |
| JP | 2002-155273 A | 5/2002 |
| JP | 2007-319359 A | 12/2007 |
| JP | 2011-67551 A | 4/2011 |
| JP | 2013-208333 A | 10/2013 |
| JP | 2015-84949 A | 5/2015 |
| KR | 10-2011-0091850 | 8/2011 |
| RU | 2 497 487 C2 | 4/2001 |
| RU | 2 202 999 C2 | 4/2003 |

OTHER PUBLICATIONS

International Search Report dated Sep. 27, 2016 in PCT/JP2016/070060 filed Jul. 7, 2016.

* cited by examiner

Fig.2(a)Exothermic warmer according to the present invention
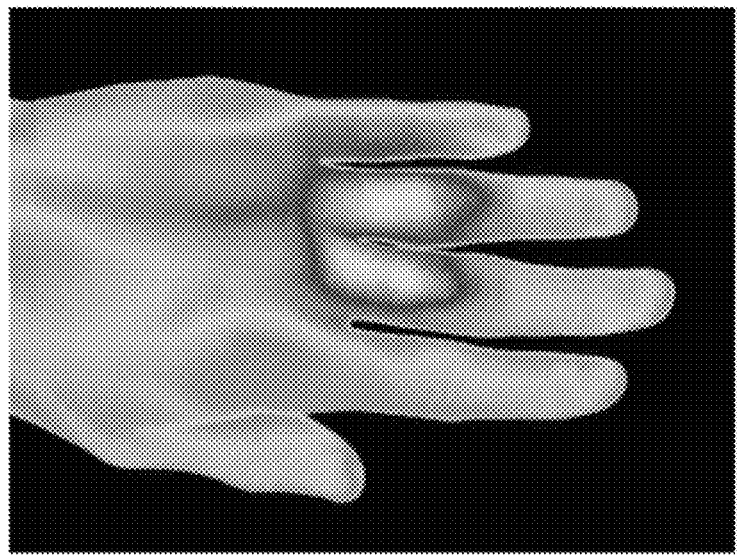
Fig.2(b)Conventional exothermic warmer
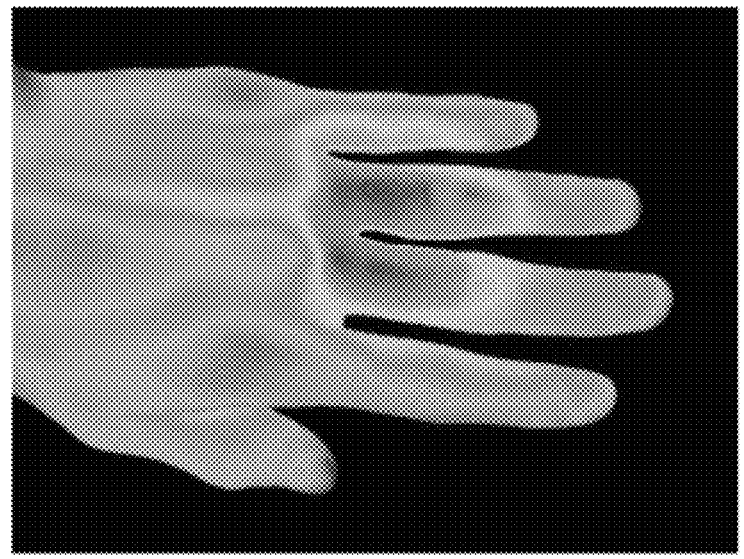

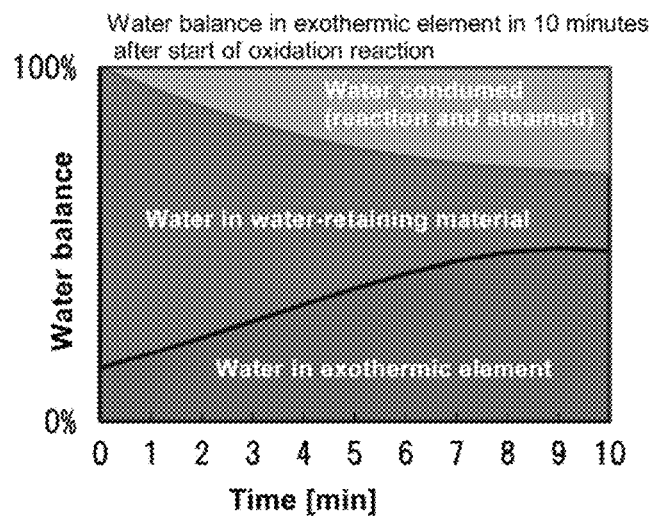
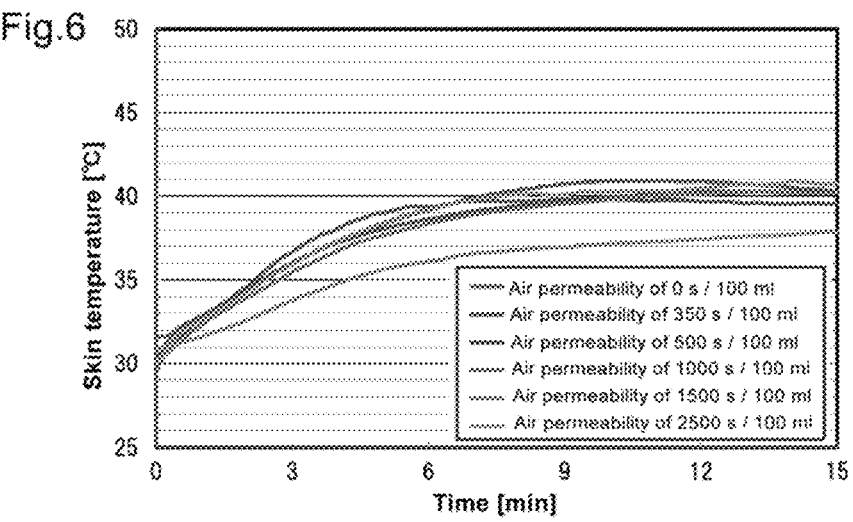

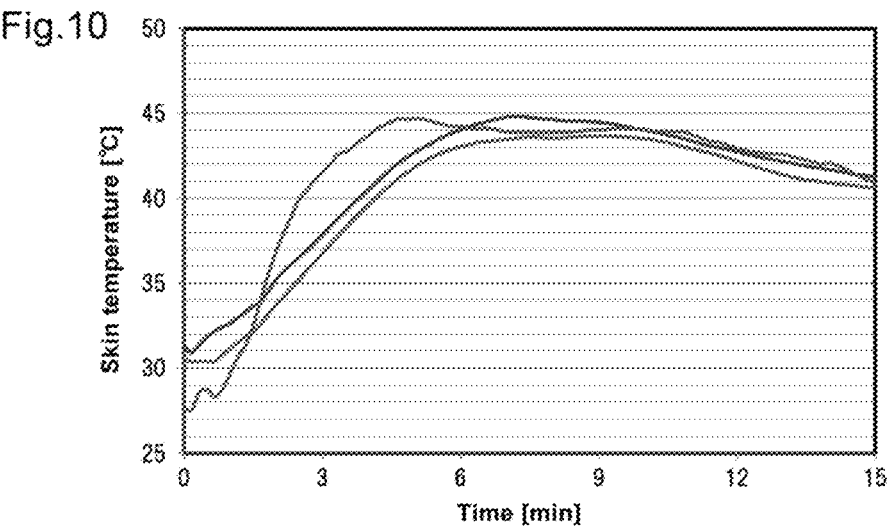

HEAT IMPLEMENT AND METHOD FOR MANUFACTURING SAME

TECHNICAL FIELD

The present invention relates to an exothermic warmer and a method for manufacturing the same.

BACKGROUND ART

Conventionally, exothermic elements in which an exothermic composition is housed in an air permeable covering material are widely used to warm a human body. For example, Patent Literature 1 discloses a steam exothermic element in which a powdered exothermic composition is housed in a highly air permeable bag member. In order to emit steam at a safe temperature from the steam exothermic element, the steam exothermic element is configured such that a temperature controlling material is provided between the exothermic composition and the bag member so as to provide a space between the steam exothermic element and the skin of the wearer, whereby the temperature of the steam that comes into contact with the skin is adjusted to 40° C. or more and 45° C. or less.

Patent Literatures 2 to 4 propose thin exothermic elements. These patent literatures disclose exothermic elements having a structure in which a stack including an exothermic composition slurry on a substrate sheet is covered with a covering material. The patent literatures also disclose that a water absorbing layer containing a water-retaining material is provided on the exothermic composition. In particular, Patent Literature 4 proposes a flexible and stretchable exothermic element that provides a sense of fit to the body surface by applying an exothermic composition slurry onto a covering material that is made of a highly air permeable non-woven fabric.

Aside from these techniques, in order to prevent excessive heat generation that can be caused by a large amount of exothermic composition being filled into one exothermic element for some reason or by a large amount of exothermic composition being unevenly distributed and concentrated in a particular area when an exothermic element is manufactured, the inventors of the present invention have proposed an exothermic element in which a water-retaining layer composed of a water-retaining sheet is stacked onto an exothermic layer so as to control the amount of water in the water-retaining layer (see Patent Literature 5).

CITATION LIST

Patent Literature

Patent Literature 1: EP 1147752 A1
Patent Literature 2: JP H9-75388 A
Patent Literature 3: JP 2002-155273 A
Patent Literature 4: JP 2007-319359 A
Patent Literature 5: US 2014/373828 A1

SUMMARY OF INVENTION

As disclosed in the patent literatures mentioned above, most conventional exothermic elements that warm the human body utilize heat generated through an oxidation reaction of an oxidizable metal such as iron. The temperature control in the exothermic elements is performed by adjusting: (1) the amounts of an oxidizable metal, an electrolyte serving as a reaction aid, a carbon component, and water; (2) the mass of exothermic composition per product; or (3) the amount of oxygen supplied to the exothermic composition. However, the manufactured exothermic elements have significantly different exothermic temperatures due to raw material variations and manufacturing variations. For safety reasons, the occurrence of variations in the exothermic temperature of an exothermic element provided for a user has to be avoided as much as possible.

According to the technique disclosed in Patent Literature 1, the exothermic temperature is managed with the use of temperature adjusting means that provides a physical distance between the exothermic layer and the skin of the wearer. However, due to the physical distance, the exothermic element inevitably becomes thick, which affects wearing comfort and fit. Particularly when the exothermic warmer is applied to an uneven area such as the face or the vicinity of a joint, there is room for improvement regarding fit.

The techniques disclosed in Patent Literatures 2 to 4 are techniques for implementing a thin exothermic element, but neither of the patent literatures gives consideration to temperature adjustment. In particular, Patent Literature 4 discloses that, with the technique of Patent Literature 4, steam is generated at a temperature in the range of 40° C. or more and 50° C. or less. Due to this, the exothermic element disclosed in Patent Literature 4 may cause disadvantages such as failing to provide a sense of warmth to the user in a stable manner, and increase the risk of a low temperature burn.

Patent Literature 5 contains no disclosure as to adjustment of the temperature of generated steam. The highest temperature of the exothermic elements disclosed in the examples of Patent Literature 5 is about 58° C.

In view of the above, it is an object of the present invention to provide an exothermic warmer with which it is possible to easily obtain a comfortable sense of warmth while ensuring a good fit.

The present invention provides an exothermic warmer including: an exothermic warmer main body that generates heat through an oxidation reaction and in which a flat-shaped exothermic element containing an oxidizable metal, an electrolyte, a carbon component, and water is covered with a first cover sheet and a second cover sheet. The first cover sheet is a sheet that is air permeable and does not substantially limit the oxidation reaction. A water-retaining material is provided so as to be at least partially in contact with the exothermic element. The exothermic warmer satisfies conditions (A) to (C) given below:

(A) a difference between an internal temperature of the exothermic element and a highest surface temperature of the exothermic warmer main body is 10° C. or less;

(B) a highest skin temperature obtained when the exothermic warmer is applied to human skin is 38° C. or more and 42° C. or less; and (C) a ratio of an amount (mg/cm$^2$·10 min) of steam generated in 10 minutes after a start of the oxidation reaction to a mass (g/cm$^2$) of the exothermic element takes a value of 50 or more and 250 or less.

Also, the present invention provides an exothermic warmer including: an exothermic element that contains an oxidizable metal, an electrolyte, a carbon component, and water and generates heat through an oxidation reaction; and a water-absorbing polymer that is at least partially in contact with the exothermic element, the exothermic element and the water-absorbing polymer being interposed between a first cover sheet that is air permeable and does not suppress the oxidation reaction and a second cover sheet. In a state before oxidation reaction has started, the exothermic element has a water content of 9 mass % or more and 25 mass % or less, and a concentration of the electrolyte of 1 mass % or more.

Also, the present invention provides, as a preferable method for manufacturing the above-described exothermic warmer, a method for manufacturing an exothermic warmer in which an exothermic element containing an oxidizable metal, an electrolyte, a carbon component, and water is provided on a sheet. The manufacturing method includes: a step of adding the electrolyte in a solid state to one surface of the sheet; a step of applying a coating material that contains the oxidizable metal, the carbon component, and the water, but not the electrolyte; and a water-retaining material supplying step of supplying a water-retaining material to an exothermic element forming surface side of the sheet on which the exothermic element is formed. In the manufacturing method, an amount of water in the exothermic element is 9 mass % or more and 25 mass % or less.

BRIEF DESCRIPTION OF DRAWINGS

FIG. 2(a) is an image obtained using thermography for heat transfer measurement performed on a human hand to which an exothermic warmer according to the present invention has been applied, and FIG. 2(b) is an image obtained using thermography for heat transfer measurement performed on a human hand to which a conventional exothermic warmer has been applied.

FIG. 5 is a graph showing a water balance of the exothermic element in the exothermic warmer according to the present invention in 10 minutes after the start of an oxidation reaction.

FIG. 6 shows skin temperature characteristics observed in Examples 1 to 5 and Comparative Example 2.

FIG. 10 is a graph showing a skin surface temperature profile of an exothermic warmer obtained in Comparative Example 3.

DESCRIPTION OF EMBODIMENTS

Figure 1:
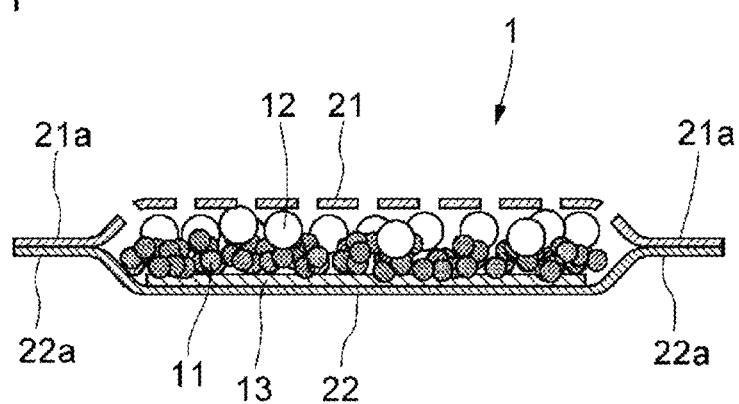
FIG. 1 is a cross-sectional view schematically showing an exothermic warmer according to a first embodiment of the present invention.

Hereinafter, the exothermic warmer according to the present invention will be described by way of preferred embodiments with reference to the drawings. FIG. 1 is a cross-sectional view schematically showing an exothermic warmer according to a first embodiment of the present invention. An exothermic warmer 1 shown in the diagram has a structure in which an exothermic element 11 having a flat shape is interposed between and covered by a first cover sheet 21 and a second cover sheet 22. The first and second cover sheets 21 and 22 constitute an outer surface of the exothermic warmer 1. The first cover sheet 21 and the second cover sheet 22 may be separate sheets, or may be one sheet that is folded over into two.

In the exothermic warmer 1, a water-retaining material 12 is disposed between the exothermic element 11 and the first cover sheet 21 so as to be in contact with the exothermic element 11. Also, a second substrate sheet 13 is disposed between the exothermic element 11 and the second cover sheet 22 so as to be in contact with the exothermic element 11. In this specification, in the exothermic warmer 1, a structural element in which the exothermic element 11 is interposed between the first cover sheet 21 and the second cover sheet 22 will be referred to as "exothermic warmer main body". Also, a structural element that includes the exothermic warmer main body and is ready to be used by the wearer will be referred to as "exothermic warmer". In the present embodiment, "exothermic warmer main body" and "exothermic warmer" refer to the same structural element, and thus, unless it is necessary to make a distinction therebetween, "exothermic warmer main body" and "exothermic warmer" will be collectively referred to as "exothermic warmer".

The first and second cover sheets 21 and 22 include extension portions 21a and 22a extending outward from the outer edges of the exothermic element 11, the water-retaining material 12, and the second substrate sheet 13. The extension portions 21a and 22a are joined to each other at their opposing surfaces. Accordingly, the exothermic element 11, the water-retaining material 12, and the second substrate sheet 13 are housed in an enclosed space formed by the two cover sheets 21 and 22. The exothermic warmer 1 configured as described above has a flat shape, and a shape as viewed in plan view according to the specific application of the exothermic warmer. Examples of the shape as viewed in plan view include a polygonal shape such as a rectangular shape, a circular shape, an oval shape, and a dumb-bell shape.

The exothermic element 11 contains an oxidizable metal, an electrolyte, a carbon component, and water. As described above, the exothermic element 11 is a layered structural element having a flat shape. The exothermic element 11 generates heat through an oxidation reaction of the oxidizable metal and provides a sufficient warming effect to the user.

The exothermic warmer 1 according to the present embodiment satisfies the following conditions:

(A) the difference between the internal temperature of the exothermic element and the highest surface temperature of the exothermic warmer 1 is 10° C. or less;

(B) the highest skin temperature obtained when the exothermic warmer 1 is applied to human skin is 38° C. or more and 42° C. or less; and (C) the ratio of the amount (mg/cm$^2 \cdot$10 min) of steam generated in 10 minutes after the oxidation reaction has started to the mass (g/cm$^2$) of the exothermic element takes a value of 50 or more and 250 or less.

Each of the conditions will be described below.

As a result of the condition (A) being satisfied, in the exothermic warmer 1 according to the present embodiment, it is unnecessary to form a large space between the exothermic element 11 and the first and second cover sheets 21 and 22 that constitute the outer surface of the exothermic warmer 1. Consequently, the thickness of the exothermic warmer 1 can be easily reduced. Accordingly, it is possible to obtain an exothermic warmer 1 with a good fit. As used herein, the term "the highest surface temperature of the exothermic warmer 1" refers to the highest temperature of a surface of the exothermic warmer 1 that is in contact with the skin.

As a result of the condition (B) being satisfied, the exothermic warmer 1 can provide an appropriate sense of warmth to human body when the exothermic warmer 1 is applied to the human body. Even when the exothermic warmer 1 is applied directly or indirectly to human body for a long time, it is possible to provide an advantageous effect of reducing the risk of a low temperature burn, in addition to an advantageous effect of providing a comfortable warmth to the user over the application time. As will be described later, the exothermic warmer 1 may be applied by bringing the exothermic warmer main body into direct contact with human skin. Alternatively, the exothermic warmer 1 may be applied by configuring the exothermic warmer 1 such that the exothermic warmer main body is covered with an outer jacket made of a material such as a non-woven fabric, and applying the exothermic warmer 1 to human skin. In the case where the exothermic warmer 1 is configured such that the exothermic warmer main body is covered with a material such as a non-woven fabric, the highest temperature defined by the condition (B) is measured with that configuration. Even in the case where skin temperature measurement is performed by removing the outer jacket from the exothermic warmer 1 so as to expose the first and second cover sheets 21 and 22, and covering the exothermic warmer 1 with a non-woven fabric bag, which will be described later, it is preferable that the exothermic warmer 1 satisfies the highest temperature range defined by the condition (B).

Furthermore, as a result of the condition (C) being satisfied, when the exothermic warmer 1 is applied to human body, a large amount of steam is supplied to the human body, which allows a sense of warmth to reach deep into the human body. Accordingly, it is possible to widely and uniformly warm the human body irrespective of the degree of contact between the human body and the exothermic warmer 1. Moreover, the exothermic warmer 1 generates a large amount of steam per unit mass of the exothermic element 11. Accordingly, with the large amount of steam, the exothermic warmer 1 can provide an appropriate sense of warmth to the human body while being lightweight and thin. Thus, the exothermic warmer 1 is also advantageous in that it can be easily applied to the vicinity of the eyes that are heat sensitive parts of the body as well as to parts of the body such as elbows and knees where the ability to follow flexion is required. In the case where the steam generated from the exothermic warmer 1 is applied to a human body, it is preferable, in particular, to apply the exothermic warmer main body so as to be in direct contact with the human skin, but the exothermic warmer main body may be covered with an outer jacket, in particular, an outer jacket made of a non-woven fabric before use. In the case where the exothermic warmer 1 is configured such that the exothermic warmer main body is covered with an outer jacket made of a material such as a non-woven fabric, the amount of steam defined by the condition (C) is measured for the exothermic warmer 1 while covered by the outer jacket. However, even in the case where the measurement is performed by removing the outer jacket so as to expose the first and second cover sheets 21 and 22 at the outermost surface, it is preferable to satisfy the range of the amount of stream defined by the condition (C).

As a result of the exothermic warmer 1 satisfying the three conditions (A) to (C), it is possible to increase the amount of steam generated per unit mass of the exothermic element 11, and uniformly warm the entire application area while achieving a thin configuration with a good fit. As a result, it is possible to suppress variations in the skin temperature as compared to a conventional exothermic warmer. Also, the exothermic warmer 1 controls the skin temperature to be in an appropriate range, and it is therefore possible to provide, to the user, a comfortable sense of warmth that is safe for use on the human body.

FIGS. 2(*a*) and 2(*b*) are images obtained through thermography, and respectively show the state of heat transfer when the exothermic warmer according to the present invention that satisfies the conditions (A) to (C) described above is applied to a human hand (FIG. 2(*a*)) and the state of heat transfer when a conventional exothermic warmer whose amount of steam generated does not satisfy the condition (C) (FIG. 2(*b*)) in a comparative manner. As is clear from the images, the exothermic warmer according to the present invention provides an appropriate temperature state uniformly over a wide range of the skin as compared to the conventional exothermic warmer.

The conditions (A) to (C) given above will be further described. With respect to the condition (A), the difference between the internal temperature of the exothermic element 11 and the highest surface temperature of the exothermic warmer 1 is preferably 9° C. or less, and more preferably 8° C. or less from the viewpoint of safety and the exothermic efficiency of the exothermic element 11 to emit heat, as well as from the viewpoint of the thickness and flexibility of the exothermic element 11. As used herein, the difference between the internal temperature of the exothermic element 11 and the highest surface temperature of the exothermic warmer 1 refers to a value calculated from the following expression:

Internal temperature of exothermic element 11−Highest surface temperature of exothermic warmer 1.

In the case where the internal temperature of the exothermic element 11 is excessively high, there is a risk of skin burn if heat emitted from the exothermic element 11 is transferred directly to the human body. Accordingly, it is necessary to control the surface temperature of the exothermic warmer 1 by interposing a heat insulating material between the exothermic element 11 and the human body or providing a gap therebetween. With the exothermic warmer 1 configured such that a heat insulating material is interposed between the exothermic element 11 and the human body or a gap is provided therebetween, the thickness of the exothermic element 11 increases and flexibility decreases. In addition, there are other disadvantages such as the manufacturing process becoming complex as well as an increase in cost. Furthermore, heat is generated in an amount more than necessary, and energy other than the heat applied to the human body is wasted. Accordingly, the efficiency of heat applied to the human body is insufficient with respect to the amount of heat generated. The internal temperature T1 of the exothermic element 11 and the highest surface temperature T2 of the exothermic warmer 1 may be set to satisfy T1>T2, or may be set to satisfy T1<T2. Ordinarily, the internal temperature T1 of the exothermic element 11 and the highest surface temperature T2 of the exothermic warmer 1 are set to satisfy T1>T2 in terms of ease of control.

In the exothermic warmer 1, the inside of the exothermic element 11 refers to a center in the thickness direction at a position of a central portion of the contact surface between the exothermic element 11 and the water-retaining material 12 as viewed in plan view. Also, the internal temperature of the exothermic element 11 is measured by inserting a K-type thermocouple into the exothermic element 11. Also, the highest surface temperature of the exothermic warmer 1 refers to the temperature at a center position on the outer surface of the first cover sheet 21 of the exothermic warmer 1. The highest surface temperature of the exothermic warmer 1 is measured by bringing a K-type thermocouple into contact with the center position on the outer surface of the first cover sheet 21. The measurement is performed in an atmosphere at 20° C. and 65% RH. The temperature difference between the highest internal temperature of the exothermic element 11 and the highest surface temperature of the exothermic warmer 1 measured in that atmosphere is calculated. The difference between the internal temperature of the exothermic element 11 and the highest surface temperature of the exothermic warmer 1 measured in the manner described above is preferably 9° C. or less, more preferably 8° C. or less, and even more preferably 6° C. or less. The lower limit value for this difference is preferably as low as possible, and most preferably 0° C.

With respect to the condition (B), the highest skin temperature obtained when the exothermic warmer is applied to human skin is measured by using a thermistor-equipped data logger (LT-8 available from Nikkiso Therm Co., Ltd.). The measurement is performed by fixing the thermistor to a human skin surface such as the upper eyelid by using surgical tape. In the case where the measurement is performed in the absence of the influence of the outer jacket, the exothermic element main body from which the outer jacket has been removed is covered with a bag made of a non-woven fabric before being measured. The non-woven fabric used at this time is a combination of an air-through non-woven fabric and a needle-punched non-woven fabric used in examples, which will be described later. The highest skin temperature measured in this way is, as described above, preferably 38° C. or more and 42° C. or less, more preferably 38.5° C. or more and 41.5° C. or less, and even more preferably 39° C. or more and 41° C. or less.

Figure 3:
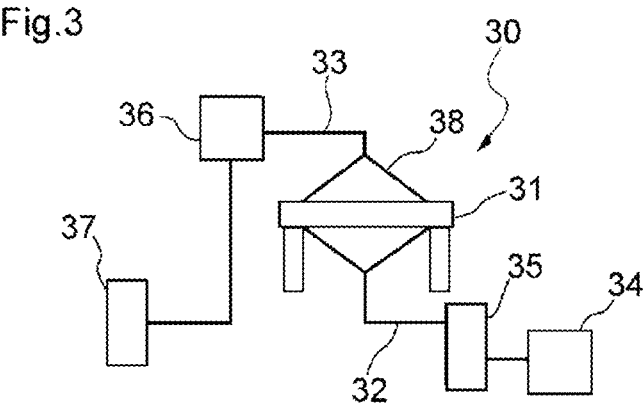
FIG. 3 is a schematic diagram showing an apparatus for measuring the amount of steam generated.

With respect to the condition (C), the amount of steam generated in 10 minutes after the oxidation reaction started was measured in the following manner by using an apparatus 30 shown in FIG. 3. The apparatus 30 shown in FIG. 3 includes a measurement chamber (with a volume of 2.1 L) 31 that is made of aluminum, an inflow channel 32 through which dehumidified air (with a humidity of less than 2% at a flow rate of 2.1 L/min) is allowed to flow into below the measurement chamber 31, and an outflow channel 33 through which air is discharged from above the measurement chamber 31. The inflow channel 32 is equipped with an inlet temperature-humidity meter 34 and an inlet flow rate meter 35. On the other hand, the outflow channel 33 is equipped with an outlet temperature-humidity meter 36 and an outlet flow rate meter 37. The measurement chamber 31 is equipped with a thermometer (thermistor) 38. As the thermometer 38, a thermometer having a temperature resolution of about 0.01° C. is used. At a measurement environment temperature of 30° C. (30±1° C.), the warmer is taken out of the packaging material, and placed on the measurement chamber 31 with its steam emitting surface facing upward. Then, the thermometer 38 with a metal sphere (4.5 g) is placed on the warmer. In this state, dehumidified air is allowed to flow from below the measurement chamber 31. Based on the temperatures and humidity levels measured by the inlet temperature-humidity meter 34 and the outlet temperature-humidity meter 36, the difference in absolute humidity between before and after air is allowed to flow into the measurement chamber 31 is obtained. Furthermore, based on the flow rates measured by the inlet flow rate meter 35 and the outlet flow rate meter 37, the amount of steam emitted from the warmer is calculated. A detailed description of this apparatus is given in JP 2004-73688A that is an earlier application of the applicant of the present invention. The amount of steam is calculated by using the following expression.

$$U = e/es \times 100$$ [Math. 1]
$$D = \frac{0.794 \times 10^{-2}}{1 + 0.00366t} \times \frac{U}{100} \times es$$
$$P = 2.1 \times S / 60$$
$$A = P \times D / 1000$$

where U (% RH) represents relative humidity, e (Pa) represents steam pressure, es (Pa) represents saturated steam pressure, D (g/m$^3$) represents absolute humidity, P (l) represents unit air volume, S (s) represents sampling period, and A (g) represents the amount of steam.

Also, with respect to the condition (C), the mass of the exothermic element 11 refers to the total mass of the oxidizable metal, the electrolyte, the carbon component, and water. The mass of water includes the mass of water contained in the water-retaining material 12. Also, if the exothermic element 11 contains a component(s) other than the above components, the mass of the component(s) is also included. The mass of the exothermic element 11 is obtained by measuring the mass of a sheet in the step of stacking the exothermic element 11 on the sheet, again measuring the mass of the sheet after the exothermic element 11 has been stacked on the sheet, and then calculating the difference between before and after the exothermic element 11 is stacked on the sheet. The value calculated from the amount of steam (mg/cm$^2$·10 min) and the mass of the exothermic element 11 (g/cm$^2$) measured in the manner described above is, as described above, 50 or more and 250 or less, preferably 60 or more and 240 or less, more preferably 70 or more and 230 or less, and even more preferably 80 or more and 220 or less. If the generation of steam ends before 10 minutes has elapsed, the amount of steam generated until the end of the generation is measured, which is regarded as the amount of steam generated in 10 minutes, and the amount of steam per mass of the exothermic element 11 is calculated. The value obtained at this time is preferably within the above-described range. In the exothermic warmer 1, it is preferable that the steam generation period is 10 minutes or more, and the amount of steam generated during the steam generation period is within the above-described range because an appropriate skin temperature can reach deep into the skin. In particular, the steam generation period is preferably 15 minutes or more, and more preferably 20 minutes or more. As used herein, the steam generation period refers to the period of time from the start of the reaction to the end of the reaction.

The inventors of the present invention have found that, in order to realize the three conditions (A) to (C) in the exothermic warmer 1 according to the present embodiment, the following conditions are very effective: (1) oxygen is supplied in an amount that does not hinder the oxidation reaction of the oxidizable metal contained in the exothermic element 11; and (2) the amount of water contained in the exothermic element 11 is controlled to an appropriate level. Hereinafter, the conditions (1) and (2) will be described.

First, the condition (1) will be described. Ordinarily, among the causes of temperature variations in the exothermic warmer, (i) the amount of raw material and (ii) the mass of each exothermic warmer 1 can be controlled with high accuracy by using highly accurate measurement equipment. However, (iii) the amount of oxygen supplied is dependent on the amount of air permeation of the air permeable sheet that constitutes the outer surface of the exothermic warmer, and it is therefore not easy to manage the amount of air permeation of the air permeable sheet with high accuracy. Accordingly, it is necessary to accept a certain amount of variation.

In general, as the air permeable sheet, a sheet having fine pores (hereinafter referred to as a microporous sheet) formed by extruding and drawing a resin blended with calcium carbonate in a melted state is known. Other than this, various types of sheets are known such as a sheet perforated using a heated stylus, a sheet in which a plurality of non-woven fabric sheets are stacked, and a sheet manufactured by a melt blown method. Among them, a microporous sheet is often used as the cover sheet of a commercially available exothermic warmer because the pore density can be adjusted to a high level. However, in commercially available exothermic warmers including microporous sheets, despite the fact that they are on the market as having the same air permeability, the amount of air permeation varies from exothermic warmer to exothermic warmer. The variations in the amount of air permeation make it difficult to perform precise control of the exothermic temperature of conventional exothermic warmers. Accordingly, in order to eliminate the variations in the exothermic temperature caused by variations in the amount of oxygen supplied to the exothermic element, the present invention is configured such that oxygen is supplied in an excess amount over the amount of oxygen required for the oxidation reaction without limiting the supply of oxygen through the air permeable sheet, and the condition (1) given above is used. In the present invention, the expression "the first cover sheet is a sheet that is air permeable and does not substantially limit the oxidation reaction" refers to a sheet that is highly air permeable so that the exothermic warmer 1 including the first cover sheet has the same level of exothermic characteristics as the exothermic characteristics of an exothermic warmer 1 that does not include the first cover sheet.

However, when only condition (1) is used, the reaction speed in the exothermic element can increase significantly to elevate the temperature of the exothermic warmer to a high level in a short period of time, and it may be very dangerous to apply such an exothermic warmer to a human body. For safety, it is necessary to control the skin surface temperature of the skin to which the exothermic warmer is applied within a range of 38° C. or more and 42° C. or less, and when the skin surface temperature is within this temperature range, a comfortable sense of warmth can be provided to the user. If the skin temperature is less than 38° C., the user often cannot sufficiently feel a sense of warmth. This is more prominent particularly in an exothermic warmer designed to be applied for a short period of time. If, on the other hand, the skin temperature exceeds 42° C., the wearer is likely to feel that it is too hot. By controlling the skin temperature to be, in particular, 42° C. or less, it is possible to reliably reduce the risk of a low temperature burn. That is, it is necessary to provide an exothermic element in which, in a state in which the supply of oxygen through the air permeable sheet is not limited, the skin surface temperature is controlled to be within a range of 38° C. to 42° C., which is a temperature range that is safe for use on the human body and comfortable for the human body.

Figure 4:
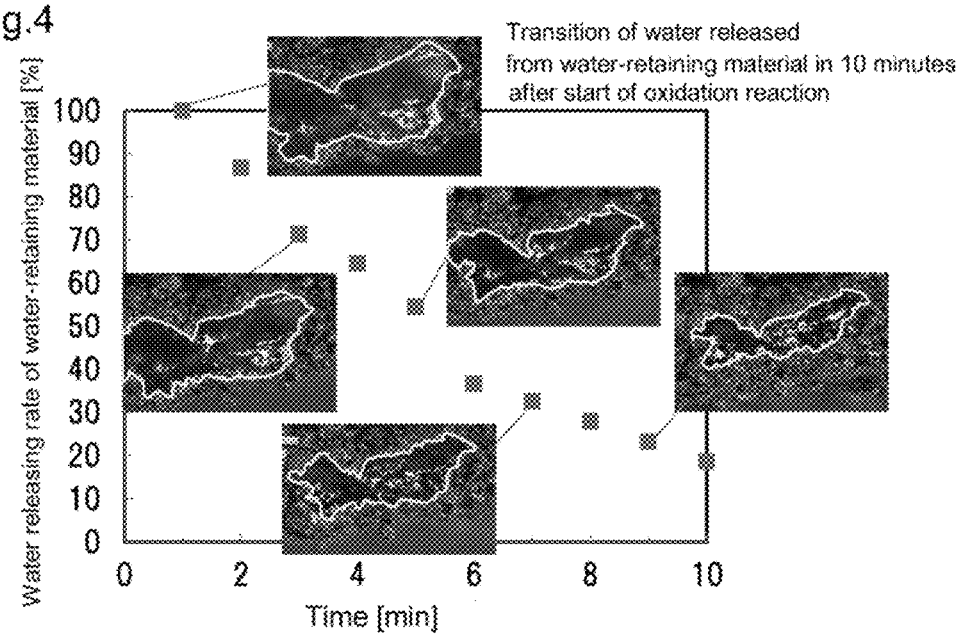
FIG. 4 is a graph showing the water releasing behavior of a water-retaining material of the exothermic warmer according to the present invention in 10 minutes after the start of an oxidation reaction.

Accordingly, the inventors of the present invention have decided to use condition (2) together with condition (1). With condition (2), even when condition (1) is used, the rate of temperature increase and the temperature characteristics of the exothermic element 11 are controlled, and it is therefore possible to provide an appropriate sense of warmth quickly when the exothermic warmer 1 is applied to a human body. The basic principle of the condition (2) is based on the fact that water, which is a substance that has a large heat capacity, is contained in the exothermic element 11 in an excess amount that vastly surpasses the amount of water required for the oxidation reaction so that the exothermic energy is consumed by the water which is thus heated during the oxidation reaction and suppress an increase in the temperature of the exothermic element 11. That is, the exothermic element 11 contains an amount of water that is larger than that in an ordinary exothermic element that performs temperature control by limiting the amount of oxygen supplied to the exothermic element 11. Also, the exothermic warmer is designed such that the amount of water in the exothermic element 11 at an initial stage of the reaction is smaller than that during the reaction, and has a structure in which the water-retaining material 12 that contains a large amount of water is disposed so as to be at least in part contact with the exothermic element so that a large amount of water is supplied from the water-retaining material 12 to the exothermic element 11. Indeed, the present inventors have found a water balance as shown in FIG. 5 by estimating the amount of water consumed by the oxidation reaction from calculation using an oxidation reaction expression, and experimental values for the mass of the exothermic element 11 and the water content in the exothermic element 11 before and after the exothermic reaction, observing changes in the water-retaining material 12 over time by using a microscope, and calculating the amount of water released from a cross-sectional area of the exothermic element 11 as shown in FIG. 4. The water contained in the exothermic element 11 is divided into two types: water that is consumed with the oxidation reaction; and water that remains in the system. Furthermore, the water consumed is divided into water that is consumed in the oxidation reaction and water that is discharged out of the system in the form of steam. The water that remains in the system is divided into water retained in the water-retaining material 12 and water retained in the exothermic element 11. As a result of the water-retaining material 12 being partially in contact with the exothermic element 11, water exchange between the water-retaining material 12 and the exothermic element 11 proceeds smoothly according to changes in the temperature of the exothermic element 11 and the electrolyte concentration in the exothermic element 11 that are associated with the oxidation reaction. Consequently, as shown in FIG. 5, a large amount of water is supplied from the water-retaining material 12 to the exothermic element 11. At an initial stage of the oxidation reaction, the water content in the exothermic element 11 is appropriately low, and thus the temperature rises quickly at the initial stage of the reaction, and a large amount of water is released from the water-retaining material 12 and supplied to the exothermic element 11 along with the temperature increase, whereby the water content in the exothermic element 11 rises above that at the initial stage of the reaction, and thus the temperature increase of the exothermic element 11 due to the exothermic reaction can be suppressed. The excess amount of water contained in the exothermic element is efficiently used in the reaction, and thus the duration of the exothermic reaction is long, as a result of which, more steam is generated.

Heat is applied to the body from the exothermic element through heat transfer due to the exothermic element being in contact with the skin and heat transfer from steam in the case where steam is generated, and it is necessary to strictly control these two types of heat transfer in order to control the skin temperature to be in the above-described temperature range. However, in order to manufacture an exothermic element with a stable exothermic temperature, strict quality control is essential in addition to an advanced manufacturing technique, and products that failed to meet the standards are discarded as defective products without being made available to consumers, resulting in a significant loss for the manufacturer. In contrast, with the exothermic warmer 1 according to the present embodiment, because the above-described configuration is used, the exothermic temperature of the exothermic element 11 can be strictly controlled.

Normally, the increase in the amount of steam generated from the exothermic element by increasing the amount of air permeation of the air permeable sheet involves a temperature increase. That is, if the amount of steam is increased, the temperature increases as well, and if the temperature increase is suppressed, the amount of steam is reduced. Thus, conventionally, an increase in the amount of steam generated and an optimal exothermic temperature are in a trade-off relationship. For this reason, a conventional exothermic warmer that is available on the market is configured to suppress the exothermic reaction by limiting the amount of air permeation of the air permeable sheet. In contrast, the present invention is configured such that the amount of air permeation of the air permeable sheet, or in other words, the amount of air permeation of the first cover sheet 21 is increased, and an excess amount of water can be supplied from the water-retaining material 12, with the initial amount of water in the exothermic element 11 being appropriately set to be low. With this configuration, both an increase in the amount of steam and an optimal exothermic temperature that were conventionally seen as incompatible were successfully achieved.

A conventional exothermic warmer is configured to warm the body by being brought into contact with the body. Accordingly, the degree of contact between the exothermic warmer and the target contact area varies depending on the size and shape of the target contact area. Also, the exothermic warmer is attached in different ways from user to user, and thus users feel warmth differently. In contrast, the exothermic warmer 1 according to the present embodiment is configured to warm the body through spatial heating that uses steam mainly by using a large amount of steam as a heating medium. Accordingly, even if the exothermic warmer comes into contact with the target area in different ways due to differences in the size and shape of the target area that vary from individual to individual, it is possible to uniformly warm the entire target area, and suppress skin temperature variations as compared to the conventional exothermic warmer.

It is preferable that the air permeability of the first cover sheet 21 of the exothermic warmer 1 is 0 sec/(100 ml·6.42 cm$^2$) or more and 1500 sec/(100 ml·6.42 cm$^2$) or less from the viewpoint of preventing the supply of oxygen from being the rate-determining step in the exothermic reaction. As used herein, the term "air permeability" refers to a numerical index based on the Gurley (JIS P8117) measurement method, and is defined by the time during which 100 ml of air passes through an area of 6.42 cm$^2$ under a constant pressure. When the first cover sheet 21 has an air permeability of 1500 sec/(100 ml·6.42 cm$^2$) or less, it means that the time required for 100 ml of air to pass therethrough is 1500 seconds or less, and the greater the value, the smaller the amount of air permeation of the first cover sheet, and conversely, the smaller the value, the greater the amount of air permeation of the first cover sheet. Accordingly, because the state under the Gurley measurement method and the state in which the exothermic element is actually used are not necessarily the same, even if a numerical value is obtained using the Gurley measurement method, this does not necessarily mean that the first cover sheet 21 will hinder the supply of oxygen to the exothermic element 11. The preferred air permeability range varies depending on the composition of the exothermic element 11, the initial amount of water, and the like, but it is better to have lower air permeability. To be specific, the air permeability is preferably 1200 sec/(100 ml·6.42 cm$^2$) or less, more preferably 1000 sec/(100 ml·6.42 cm$^2$) or less, and even more preferably 500 sec/(100 ml·6.42 cm$^2$) or less. An air permeability within an above range is preferable because the exothermic reaction is unlikely to be affected by the external environment, and the amount of steam generated and temperature control can be easily balanced.

Through experiments, the inventors of the present invention have selected a range that prevents the supply of oxygen from being the rate-determining step in the oxidation reaction, and specified an air permeability range. FIG. 6 shows profiles obtained in Examples 1 to 5 and Comparative Example 2, which will be described later, the profiles showing an increase in the temperature of exothermic elements to the highest temperature, the exothermic elements each obtained by placing a flat-shaped exothermic element made of the same exothermic composition in a bag made of a microporous sheet having a different air permeability and sealing its end portions. For comparison, a result obtained by using an exothermic element whose air permeability is not limited at all, or in other words, an exothermic element having an air permeability of 0 sec/(100 ml·6.42 cm$^2$) is also shown. As can be seen from the diagram, an exothermic element having an air permeability of 1500 sec/(100 ml·6.42 cm$^2$) or less has the same highest temperature as that of the exothermic element having an air permeability of 0 sec/(100 ml·6.42 cm$^2$), from which it is understood that the amount of oxygen required for the exothermic reaction is supplied to the inside of the exothermic composition without the supply of oxygen being hindered. With respect to an exothermic element having an air permeability of 2500 sec/(100 ml·6.42 cm$^2$) or more, the profile was delayed and the highest temperature was low, from which it was understood that it was affected by the hindrance of air permeation. Accordingly, it can be said that a microporous sheet having an air permeability of 1500 sec/(100 ml·6.42 cm$^2$) or less is in a so-called free air permeation state in which the air permeability is not restricted, from the viewpoint of the oxidation reaction of the exothermic element.

The first cover sheet 21 according to the present embodiment is preferably moisture permeable to allow steam to pass therethrough. It is preferable that the first cover sheet 21 has a moisture permeability of 2000 g/(m$^2$·24 h) or more, more preferably 2500 g/(m$^2$·24 h), and even more preferably 3000 g/(m$^2$·24 h) or more. If the first cover sheet 21 has a moisture permeability of 2000 g/(m$^2$·24 h) or more, water is unlikely to accumulate within the exothermic warmer 1 according to the present embodiment that has a feature of generating a large amount of steam, and it is therefore possible to eliminate a cause that hinders the exothermic reaction. In particular, a moisture permeability of 2500 g/(m$^2$·24 h) or more, and more particularly a moisture permeability of 3000 g/(m$^2$·24 h) is preferable because steam is smoothly emitted to the outside of the exothermic warmer 1, and the warming effect is likely to reach deep into the skin of the wearer. The moisture permeability is measured in accordance with JIS Z0208.

Because in the exothermic warmer 1, air permeation control that suppresses the oxidation reaction is not performed, it may be, in principle, ideal to not use the first cover sheet 21. However, it is necessary to prevent the constituent materials of the exothermic element 11 from leaking to the outside, and thus in practice, the first cover sheet 21 is required.

In particular, the exothermic element 11 contains water, and thus, from the viewpoint of preventing water other than steam from leaking to the outside, the first cover sheet 21 preferably has a water pressure resistance of 1500 mmH$_2$O or more, more preferably 2000 mmH$_2$O or more, and even more preferably 3000 mmH$_2$O or more. From the viewpoint of water impermeability, it is unnecessary to set the upper limit value for the water pressure resistance. With a water pressure resistance within an above range, particularly when the exothermic warmer 1 is used in the vicinity of the eyes, it is possible to prevent water from entering the eyes together with the components of the exothermic element 11, and thus the exothermic warmer 1 can be used comfortably and safely. This configuration is preferable particularly when a system is used in which an alkaline component elutes into water due to the oxidation reaction. The water pressure resistance is measured by using a measurement method that conforms to JIS L1092, and it is possible to use, for example, a water pressure resistance tester FX3000 available from TEXTSET.

From the above, the first cover sheet 21 is preferably a sheet that is water impermeable but does not hinder the permeation of oxygen and steam. Such a sheet can be selected from among a sheet made of a porous material, a sheet made of a non-porous material, a sheet made of a coating material, and the like. Among these, in terms of cost, it is preferable to use a sheet made of a porous material. For example, it is preferable to use a moisture permeable sheet made of a microporous film from the viewpoint of achieving both making the exothermic warmer 1 thinner and strength during use. A moisture permeable sheet made of a microporous film is a sheet that allows air to pass therethrough but does not allow water to pass therethrough, the sheet being obtained by extruding, through a die, a melted resin in which fine particles of calcium carbonate or the like are kneaded into a polyolefin resin such as polyethylene so as to form a sheet, and uniaxially or biaxially drawing the formed sheet so as to debond the interface between the calcium carbonate and the resin to form a fine porous communication portion.

The first cover sheet 21 may be a sheet other than the moisture permeable sheet made of a microporous film as long as the sheet is a sheet that does not allow water to pass therethrough but allows oxygen and steam to pass therethrough and in which consideration is given to leakage resistance. As the first cover sheet 21, it is possible to use, for example, a woven fabric, a non-woven fabric, paper, synthetic paper, or the like obtained by mixing one or more selected from artificial fibers made of polyamide, vinylon, polyester, rayon, acetate, acrylic resin, polyethylene, polypropylene, poly(vinyl chloride), and the like, and natural fibers made of pulp, cotton, hemp, silk, animal hair, and the like. Alternatively, it is also possible to use, as the first cover sheet 21, a moisture/air impermeable film or sheet, for example, a porous film or sheet made of polyethylene, polypropylene, polyamide, polyester, poly(vinyl chloride), poly(vinylidene chloride), polyurethane, polystyrene, saponified ethylene vinylacetate copolymer, ethylene vinylacetate copolymer, natural rubber, reclaimed rubber, synthetic rubber, or the like.

With respect to the second cover sheet 22 that is another sheet that constitutes the outer surface of the exothermic warmer 1 according to the present embodiment, there is no particular limitation on its air permeability and moisture permeability. The second cover sheet 22 may be air permeable or may be air impermeable. In the case where the second cover sheet 22 is air permeable, the exothermic warmer 1 is permeable on both sides. In the case where the second cover sheet 22 is air impermeable, the exothermic warmer 1 is permeable on one side, with only the first cover sheet 21 being air permeable. In the present invention, "impermeable" refers to an air permeability measured using the Gurley method of 100000 sec/(100 ml·6.42 cm$^2$) or more. In the case where the second cover sheet 22 is air permeable, the same type of sheet as the first cover sheet 21 can be used as the second cover sheet 22. In this case, the air permeability of the second cover sheet 22 may be the same as that of the first cover sheet 21, or may be greater or smaller than the air permeability of the first cover sheet 21. On the other hand, in the case where the second cover sheet 22 is air impermeable, the second cover sheet 22 is, for example, a film or sheet made of a material such as any of various types of resin or rubber.

The exothermic element 11 located between the first cover sheet 21 and the second cover sheet 22 is made of an exothermic composition containing a plurality of components. As described above, oxidizable metal particles, an electrolyte, a carbon component, and water are used as the components that constitute the exothermic composition.

In the exothermic warmer 1 according to the present embodiment, an outer jacket may be provided on the outer side of the first cover sheet 21 and/or the second cover sheet 22 that constitute the exothermic warmer main body. In the exothermic warmer main body, using water-resistant films or sheets as the cover sheets 21 and 22 may be unfavorable in terms of texture. Particularly when water-resistant films are used, there is room for improvement in terms of softness and usability. Accordingly, it is preferable to provide an outer jacket for improving texture at least on a side that is to come into contact with the skin of the wearer. For example, it is preferable that the first cover sheet 21 is located on a skin contact side that comes into contact with the skin of the wearer relative to the second cover sheet 22, and the outer jacket is provided on the skin contact side relative to the first cover sheet 21. Note that, however, in the case where the outer jacket is provided on the skin contact side relative to the first cover sheet 21, a situation must be avoided in which the outer jacket hinders the air permeability and the oxidation reaction is limited. From this viewpoint, specifically, it is preferable to use a non-woven fabric as the outer jacket that is provided on the skin contact side relative to the first cover sheet 21. Also, in terms of texture, it is preferable to use a non-woven fabric or a woven fabric as the outer jacket that is provided on the non-skin contact side relative to the second cover sheet 22. On the other hand, in terms of design, it is possible to use a sheet material including a printed film material, or a laminate thereof. In the case where an outer jacket is provided, the exothermic warmer 1 has a structure in which the outer jacket covers the exothermic warmer main body in which the exothermic element 11 is provided between the first cover sheet 21 and the second cover sheet 22 that are provided as the outermost portions of the exothermic warmer main body.

As the oxidizable metal, a metal that generates oxidation reaction heat is used. For example, it is possible to use powders or fibers made of one or more of iron, aluminum, zinc, manganese, magnesium, and calcium. Among these, it is preferable to use iron, and more preferably iron powders in terms of ease of handling, safety, manufacturing costs, storability, and stability. Examples of iron powders include reduced iron powders and atomized iron powders.

In the case where the oxidizable metal is in the form of a powder, from the viewpoint of an efficient oxidation reaction, the powder preferably has an average particle size of 10 μm or more, and more preferably 20 μm or more. Also, the powder preferably has an average particles size of 200 μm or less, and more preferably 150 μm or less. To be specific, the average particle size of the oxidizable metal particles is preferably 10 μm or more and 200 μm or less, and more preferably 20 μm or more and 150 μm or less. The particle size of the oxidizable metal refers to the maximum (particle) length when the oxidizable metal is in the form of a powder, and is measured by, for example, classification using a sieve, a dynamic light scattering method, a laser diffraction method, or the like.

The oxidizable metal content in the exothermic element 11 is, in terms of basis weight, preferably 100 $g/m^2$ or more, more preferably 200 $g/m^2$ or more, and preferably 3000 $g/m^2$ or less, and more preferably 1500 $g/m^2$ or less. To be specific, the oxidizable metal content is, in terms of basis weight, preferably 100 $g/m^2$ or more and 3000 $g/m^2$ or less, and more preferably 200 $g/m^2$ or more and 1500 $g/m^2$ or less. With the above-described ranges, it becomes easy to control the exothermic temperature of the exothermic element 11. The iron powder content in the exothermic element 11 can be obtained through an ash test according to JIS P8128, or by using a thermal gravimetric analyzer. It is also possible to determine the iron powder content by using other methods such as a vibrating sample magnetometry test that utilizes a property of causing magnetization through the application of external magnetic fields.

The carbon component has at least one of the following functions: a water-retaining function, an oxygen supply function, and a catalytic function, and preferably has all three functions. As the carbon component, for example, it is possible to use one or more selected from activated carbon, acetylene black, and graphite. Among these, activated carbon is preferably used from the viewpoint of easily attracting oxygen when wet, and maintaining a constant amount of water in the exothermic element 11. It is more preferable to use fine powders or granules made of one or more selected from coconut shell carbon, powdered charcoal, and peat carbon. Among these, it is preferable to use powdered charcoal because the amount of water in the exothermic element 11 can be easily kept in an intended range.

In terms of maintaining the amount of water contained in the water-retaining material 12 in the intended range in addition to the fact that the carbon component is uniformly mixed with the oxidizable metal, the carbon component preferably has an average particle size of 10 μm or more, and more preferably 12 μm or more, and preferably 200 μm or less, and more preferably 100 μm or less. To be specific, the carbon component has an average particle size of 10 μm or more and 200 μm or less, and more preferably 12 μm or more and 100 μm or less. The average particle size of the carbon component refers to the average of the maximum lengths (particles) when the carbon component is in the form of a powder and is measured using a dynamic light scattering method, laser diffraction method, or the like. The carbon component is preferably in the form of powders, but may be in other forms such as, for example, in the form of fibers.

The carbon component content in the exothermic element 11 is preferably, with respect to 100 parts by mass of the oxidizable metal, 0.3 parts by mass or more and 20 parts by mass or less, more preferably 1 part by mass or more and 15 parts by mass or less, and even more preferably 3 parts by mass or more and 13 parts by mass or less. With the above-described ranges, it is possible to accumulate, in the resulting exothermic element 11, water in an amount required to sustain the oxidation reaction. Also, oxygen is sufficiently supplied to the exothermic element 11, and thus an exothermic element 11 having high exothermic efficiency is obtained.

The carbon component content in the exothermic element 11 is, in terms of basis weight, preferably 4 $g/m^2$ or more, and more preferably 7 $g/m^2$ or more, and preferably 290 $g/m^2$ or less, and more preferably 160 $g/m^2$ or less. To be more specific, the carbon component content is, in terms of basis weight, preferably 4 $g/m^2$ or more and 290 $g/m^2$ or less, and more preferably 7 $g/m^2$ or more and 160 $g/m^2$ or less.

The exothermic element 11 may contain, other than the carbon component, a component having the same function, or in other words, a water-retaining function and the like. Such a component can be, for example, one or more selected from vermiculite, sawdust, and silica gel. In the case where the exothermic element 11 contains another component as mentioned above, the proportion of the carbon component with respect to the total amount of the other component and the carbon component is preferably 90 mass % or more in terms of controlling the amount of water in the exothermic element 11, more preferably 95 mass % or more, and even more preferably 98 mass % or more.

The electrolyte contained in the exothermic element 11 is used for the purpose of increasing the reaction efficiency of the oxidizable metal as well as reaction promotion for sustaining the oxidation reaction. By using the electrolyte, the oxide film of the oxidizable metal is broken, and the oxidation reaction can be accelerated. As the electrolyte, for example, it is possible to use one or more selected from an alkali metal, a sulfate of an alkaline earth metal, and a chloride. Among these, in terms of excellent electroconductivity, chemical stability, and production cost, it is preferable to use one or more selected from: various chlorides including sodium chloride, potassium chloride, calcium chloride, magnesium chloride, ferrous chloride, and ferric chloride; and sodium sulfate.

The concentration of the electrolyte in the exothermic element 11 before the start of the oxidation reaction is preferably 1 mass % or more, more preferably 3 mass % or more, and even more preferably 4 mass % or more, and preferably 20 mass % or less, more preferably 15 mass % or less, and even more preferably 10 mass % or less. To be specific, it is preferable that the concentration of the electrolyte is 1 mass % or more and 20 mass % or less, more preferably 3 mass % or more and 15 mass % or less, and even more preferably 4 mass % or more and 10 mass % or less. With the above-described range, at the time when the oxidation reaction of the exothermic element 11 is started and the water in the exothermic element 11 is consumed, an excess amount of water is rapidly supplied from the water-retaining material, specifically, a water-absorbing polymer, to the exothermic element 11, and the temperature of the exothermic element 11 and the amount of steam generated during the oxidation reaction are maintained at very favorable levels. From the viewpoint of water absorbency and water releasing properties, it is preferable to use a water-absorbing polymer with high salt tolerance as the water-retaining material. Particularly when the electrolyte content is 3 mass % or more, a high level of water absorbency is exhibited before the oxidation reaction and at a specific salt concentration, and at the same time, water is released with an increase in the salt concentration due to the oxidation reaction, and thus water control suitable for the oxidation reaction is likely to be performed. The reason is for this is that an osmotic pressure difference is likely to occur between the exothermic element 11 and the water-absorbing polymer, and the supply of water from the water-absorbing polymer to the exothermic element 11 is likely to be smooth not only at the start of the oxidation reaction but also during the oxidation reaction.

In a state before the oxidation reaction has started, the proportion of the electrolyte with respect to the total of the water content and the electrolyte content in the exothermic element 11 is preferably 5 mass % or more, and more preferably 10 mass % or more, and from the viewpoint of sufficient water retention in the water-absorbing polymer, preferably 50% mass % or less, and more preferably 40% mass % or less. To be more specific, the electrolyte content with respect to the total of the water content and the electrolyte concentration in the exothermic element 11 is preferably 5 mass % or more and 50 mass % or less, and more preferably 10 mass % or more and 40 mass % or less. The above-described ranges are preferable because the exothermic reaction of the exothermic element 11 is likely to be smooth, and water is likely to be rapidly supplied to the exothermic element when a water-absorbing polymer is used as the water-retaining material.

Also, the electrolyte content in the exothermic element 11 before the start of the oxidation reaction is, with respect to 100 parts by mass of the oxidizable metal, preferably 1 part by mass or more and 20 parts by mass or less, more preferably 2 parts by mass or more and 19 parts by mass or less, and even more preferably 3 parts by mass or more and 18 parts by mass or less. With the above-described range, the promotion of the oxidation reaction of the oxidizable metal can be maintained in a favorable manner.

The electrolyte content in the exothermic element 11 is, in terms of basis weight, preferably 5 $g/m^2$ or more, and more preferably 10 $g/m^2$ or more, and preferably 80 $g/m^2$ or less, and more preferably 70 $g/m^2$ or less. More specifically, the electrolyte content is, in terms of basis weight, preferably 5 $g/m^2$ or more and 80 $g/m^2$ or less, and preferably 10 $g/m^2$ or more and 70 $g/m^2$ or less.

The exothermic element 11 contains water. Water is used not only in the oxidation reaction of the oxidizable metal, but also used as a source of steam generated by the heat created by the oxidation reaction of the oxidizable metal, and also as a coolant that cools the generated heat to an appropriate temperature. In the exothermic warmer 1 according to the present embodiment, the water-retaining material 12 is disposed so as to be in contact with the exothermic element 11, and the amount of water contained in the exothermic element 11 before the reaction is important in terms of controlling the temperature characteristics at an initial stage of the exothermic reaction. The water in the exothermic warmer 1 is retained in the exothermic element 11 and the water-retaining material 12. The water content in the exothermic element 11 before the reaction starts is preferably 9 mass % or more with respect to the exothermic element 11. With the above-described range, the oxidizable metal can be sufficiently oxidized, and a large amount of steam is likely to be generated. For the same reason, the lower limit value for the water content in the exothermic element 11 before the start of the reaction is preferably 10 mass % or more, more preferably 11 mass % or more, and even more preferably 12 mass % or more. Also, the upper limit value is preferably 25 mass % or less, more preferably 23 mass % or less, even more preferably 20 mass % or less, and much more preferably 19 mass % or less. To be specific, the water content is preferably 9 mass % or more and 25 mass % or less, more preferably 10 mass % or more and 23 mass % or less, even more preferably 11 mass % or more and 20 mass % or less, and much more preferably 12 mass % or more and 19 mass % or less. The upper limit value for the amount of water is effective for reducing the possibility of the occurrence of the problem of water leaking to the outside of the exothermic warmer 1 upon the application of an unexpected external force before the exothermic warmer 1 is used. Furthermore, the temperature rises quickly at an initial stage of the reaction, the water is rapidly supplied from the water-retaining material 12 to the exothermic element 11, and an extremely large temperature increase in the exothermic element 11 due to the subsequent exothermic reaction can be suppressed. The amount of water contained in the exothermic element 11 can be determined by a mass difference value (total amount–dry amount of water) obtained through measurement by disassembling the exothermic warmer 1 in a nitrogen environment so as to prevent the occurrence of an oxidation reaction, and then taking the exothermic element 11 out of the exothermic warmer 1 and drying the exothermic element 11. In the case where the water-retaining material 12 is present in the exothermic element 11, after measuring the dry weight of the exothermic element 11, the water-retaining material 12 is taken out from the exothermic element 11, the total mass of the water-retaining material 12 is measured, and the mass is subtracted from the aforementioned dry weight. In this way, the net mass of the exothermic element 11 can be determined. In this specification, the term "in a state before the oxidation reaction has started" refers to a state of the exothermic warmer 1 before it is used. Before being used, the exothermic warmer is usually housed in a hermetically sealed container sealed from the outside. When in use, the hermetically sealed container is opened, and the exothermic warmer is taken out of the hermetically sealed container and exposed to the outside. The hermetically sealed container is configured to have an oxygen concentration lower than that of the outside, and thus is in a state in which the oxidation reaction does not advance or the oxygen reaction is very unlikely to advance as compared to when in use. Accordingly, in that sense, the term "in a state before the oxidation reaction has started" is a state of being present in the hermetically sealed container or a state immediately after being taken out of the hermetically sealed container and exposed to a normal oxygen concentration, and thus is not limited to a state in which no oxidation reaction takes place at all.

The exothermic element 11 made of an exothermic composition containing the above-described components can be formed by applying the exothermic composition onto, for example, the first cover sheet 21 in the form of a flat layer. Alternatively, the exothermic element 11 can be formed by applying the exothermic composition onto the second substrate sheet 13 in the form of a flat layer. It is preferable that the total basis weight of the exothermic element 11 is 200 $g/m^2$ or more, and more preferably 300 $g/m^2$ or more, and preferably 2500 $g/m^2$ or less, and more preferably 2000 $g/m^2$ or less. To be more specific, the total basis weight of the exothermic element 11 is preferably 200 $g/m^2$ or more and 2500 $g/m^2$ or less, and more preferably 300 $g/m^2$ or more and 2000 $g/m^2$ or less. With the above-described range, the exothermic warmer 1 can be made thinner, and sufficient heat generation period is likely to be obtained.

As shown in FIG. 1, the water-retaining material 12 is formed as a layer between the exothermic element 11 and the first cover sheet 21. That is, the water-retaining material 12 is disposed on a surface of the exothermic element 11 that is on the first cover sheet 21 side. The water-retaining material 12 is made of a material that is capable of retaining water. In the present invention, the term "water-retaining material" refers to a material that is capable of absorbing and retaining pure water in an amount that is 5 times or more its own weight in terms of mass. As the water-retaining material, it is preferable to use a water-absorbing polymer that is a material that has very high water retention and has a property of releasing water due to changes in heat or salt concentration. The exothermic warmer 1 is configured such that, in the initial stage of the exothermic reaction, the heat capacity of the exothermic element 11 is high due to setting the water content in the exothermic element 11 to be slightly high. With this configuration, an increase in the reaction speed due to free air permeation of the first cover sheet 21 is suppressed. Also, by providing the amount of heat generated by the exothermic reaction to the water contained in the exothermic element 11, the amount of heat is consumed by an increase in the water temperature (sensible heat). In the initial stage of the exothermic reaction, because the water contained in the exothermic element 11 is used, the electrolyte concentration in the exothermic element 11 increases abruptly. This reduces the osmotic pressure in the water-absorbing polymer, and the water retained in the water-absorbing polymer is released. Also, the water-absorbing polymer has a property of easily releasing water when the temperature becomes high. Accordingly, with these two advantageous effects working in combination, water is released from the water-absorbing polymer.

Normally, when the water content in the exothermic element 11 is increased, the exothermic reaction is suppressed, and the electrolyte concentration decreases, as a result of which, the release of water from the water-absorbing polymer is reduced or stops. However, in the exothermic warmer 1, the oxidation reaction is not suppressed by the first cover sheet 21, and thus the oxidation reaction of the oxidizable metal proceeds sufficiently, and water serving as reaction water is quickly consumed. Also, along with this, a sufficient amount of heat generation is obtained, and thus the evaporation rate of water in the exothermic element 11 is high. That is, although a large amount of water is supplied from the water-absorbing polymer to the exothermic element 11, the water content in the exothermic element 11 is constantly low for the reasons described above, and thus the electrolyte concentration is maintained at a high level. As a result, water is continuously released from the water-absorbing polymer due to an osmotic pressure difference, and an excess amount of water is supplied to the exothermic element 11. Then, when the oxidation reaction starts in this state, the amount of water contained in the exothermic warmer 1 is consumed by reaction water used in the oxidation reaction and water emitted from the exothermic warmer in the form of steam, as a result of which, the salt concentration of the exothermic warmer 1 as a whole increases. Then, the consumption of water in the exothermic element 11 and the supply of water from the water-absorbing polymer to the exothermic element 11 are instantaneously repeated.

As described above, in the exothermic warmer 1 according to the present embodiment, the consumption of water and the supply of water are repeatedly performed at a high frequency, and thus the water content in the exothermic element 11 is maintained, the reaction is sustained without causing an excessive temperature increase, and the excess amount of water contained in the exothermic element 11 is efficiently converted to steam. That is, a precisely ideal exothermic state can be obtained.

As the water-absorbing polymer, it is preferable to use a hydrogel material that is capable of absorbing and retaining pure water in an amount that is 20 times or more its own weight, and is gellable. The water-absorbing polymer may be, for example, in the form of particles. The particle shape can be, for example, a spherical shape, a lump shape, a grape cluster shape, a fiber shape, or the like. The particles preferably have a particle size of 1 μm or more and 1000 μm or less, and more preferably 10 μm or more and 500 μm or less. Specific examples of the water-absorbing polymer include starch, crosslinked carboxymethylated cellulose, a polymer or a copolymer of acrylic acid or an acrylic acid alkali metal salt, poly(acrylic acid) and a salt thereof, and a polyacrylate graft polymer.

Also, the water-absorbing polymer has a retention capacity of preferably 3 times or more, and more preferably 5 times or more its own weight, with respect to an aqueous solution having the same electrolyte concentration as that in the exothermic element 11 in a state before the oxidation reaction has started. The reason is that, as a result of the water-absorbing polymer retaining a sufficient amount of water before the start of the oxidation reaction of the exothermic element 11, it is easy to set the amount of water before the oxidation reaction of the exothermic element 11 to be small, and supply a sufficient amount of water to the exothermic element 11 after the start of the oxidation reaction.

Also, in the exothermic warmer 1, in a state before the oxidation reaction has started, the water-absorbing polymer has a total water retention capacity, in terms of mass, of preferably 1 time or more, and more preferably 2 times or more of the amount of water contained in the exothermic element. As shown in FIG. 5, with the above-described range, a sufficient amount of the water contained in the water-retaining material is continuously supplied to the exothermic element, and both the oxidation reaction and the suppression of overheating are easily achieved. The upper limit value for the total water retention capacity is preferably 15 times or less, and more preferably 10 times or less because the amount of water and the electrolyte concentration in the exothermic element 11 can be easily controlled. In particular, in a state before the oxidation reaction has started, the water-absorbing polymer has a total water retention capacity, in terms of mass, of preferably 1 time or more and 15 times or less, and more preferably 2 times or more and 10 times or less of the amount of water contained in the exothermic element 11.

Figure 9:
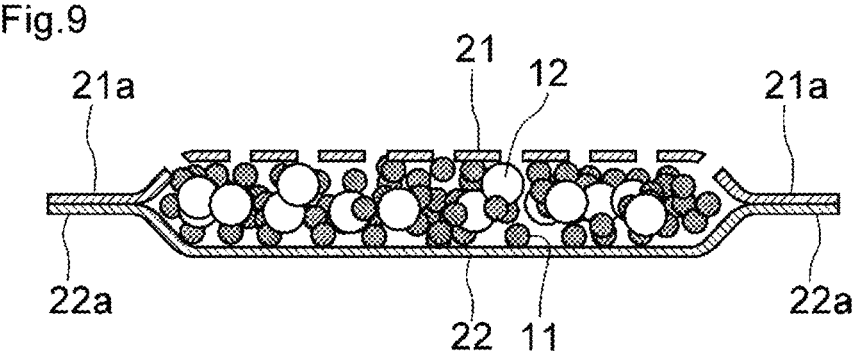
FIG. 9 is a cross-sectional view schematically showing an exothermic warmer according to a fourth embodiment of the present invention (a diagram that is equivalent to FIG. 1).

In the exothermic warmer 1 according to the present embodiment, the water-retaining material 12 may be disposed on the outside of the exothermic element 11, or may be disposed inside the exothermic element 11 as shown in FIG. 9, which will be described later. From the viewpoint of performing temperature control using water exchange between the exothermic element 11 and the water-retaining material 12, it is preferable that the water-retaining material 12 is at least partially in contact with the exothermic element 11. The responsiveness of water exchange between the exothermic element 11 and the water-retaining material 12 is enhanced as a result of the exothermic element 11 and the water-retaining material 12 being in contact with each other. Accordingly, it is preferable that the water-retaining material 12 is at least partially in contact with the exothermic element 11. It is more preferable that the contact area between the exothermic element 11 and the water-retaining material 12 is large because the responsiveness of water exchange is enhanced as the contact area increases. Specifically, it is preferable that the water-retaining material 12 is disposed in direct contact with the exothermic element 11 and there is no other member between the exothermic element 11 and the water-retaining material 12. With the above-described configuration, the water retained in the water-retaining material 12 can be supplied directly to the exothermic element 11, and it is therefore possible to generate a large amount of steam and effectively prevent the exothermic element 11 from excessively generating heat.

There is no particular limitation on the amount of the water-retaining material 12 because the liquid absorbing characteristics vary according to the form and material selected, but the amount of the water-retaining material 12 is adjusted such that the amount of water contained in the exothermic element 11 before the exothermic reaction is within a predetermined range.

In the exothermic warmer 1 according to the present embodiment, the second substrate sheet 13 disposed between the exothermic element 11 and the second cover sheet 22 is used as a substrate for supporting the exothermic element 11 during formation of the exothermic element 11. Although the second substrate sheet 13 is not an essential element, providing the second substrate sheet 13 is advantageous in that by providing the second substrate sheet 13 between the exothermic element 11 and the second cover sheet 22 so as to support the exothermic element 11, the exothermic element 11 and the second cover sheet 22 are unfixed, and the flexibility is improved. The second substrate sheet 13 may be air permeable or may be air impermeable. The same type of sheet as the second cover sheet 22 can be used as the second substrate sheet 13. To be specific, it is possible to use a non-woven fabric, paper or a film, or a stack composed of two or more thereof.

In the exothermic warmer 1 according to the present embodiment, a layer made of the water-retaining material 12 is in direct contact with the first cover sheet 21, and there is no other member between the layer made of the water-retaining material 12 and the first cover sheet 21. Instead, a first substrate sheet 14 may be disposed between the layer made of the water-retaining material 12 and the first cover sheet 21, as in the embodiment shown in FIG. 7. Providing the first substrate sheet is advantageous in that the exothermic warmer 1 can be easily manufactured, which will be described later. An exothermic warmer 1 according to the embodiment shown in FIG. 7 has the same configuration as that of the exothermic warmer 1 according to the embodiment shown in FIG. 1, except that the first substrate sheet 14 is disposed between the layer made of the water-retaining material 12 and the first cover sheet 21.

Figure 7:
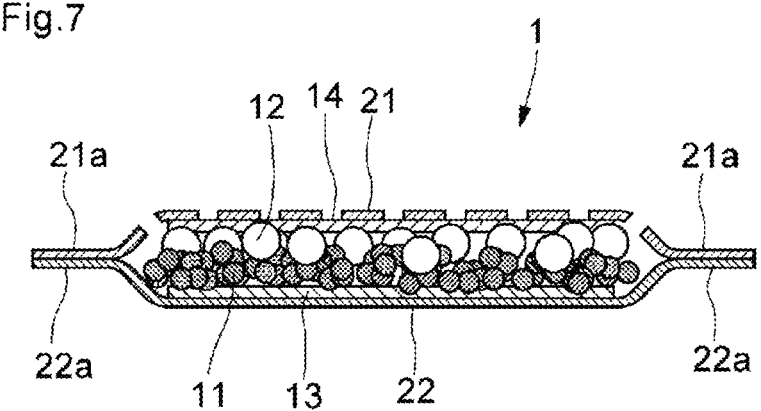
FIG. 7 is a cross-sectional view schematically showing an exothermic warmer according to a second embodiment of the present invention (a diagram that is equivalent to FIG. 1).

Unlike the second substrate sheet 13, the first substrate sheet 14 in the exothermic warmer 1 according to the embodiment shown in FIG. 7 has to be air permeable. Also, the first substrate sheet 14 is a sheet that does not substantially limit the oxidation reaction, as with the first cover sheet 21. From the viewpoints described above, the first substrate sheet 14 is preferably made of an air permeable sheet such as a non-woven fabric, paper, or a perforated film. The air permeability of the first substrate sheet 14 is preferably in the same range as that of the first cover sheet 21 described above. It is more preferable that the air permeability measured when the first cover sheet 21 and the first substrate sheet are combined together is within the same range as that of the first cover sheet 21 described above.

From the foregoing, an exothermic warmer according to a preferred embodiment of the present invention has the following configuration.

An exothermic warmer 1 including: an exothermic element 11 that contains an oxidizable metal, an electrolyte, a carbon component, and water, and generates heat through an oxidation reaction; and a water-absorbing polymer that is at least partially in contact with the exothermic element 11, the exothermic element 11 and the water-absorbing polymer being interposed between an air permeable first cover sheet 21 that does not suppress the oxidation reaction and a second cover sheet 22, wherein in a state before oxidation reaction has started, the exothermic element 11 has a water content of 9 mass % or more and 25 mass % or less, and a concentration of the electrolyte of 1 mass % or more.

The exothermic warmer 1 preferably has a thickness of 0.5 mm or more and 8 mm or less, and more preferably 1 mm or more and 6 mm or less because it is possible to easily implement a thin design with a good fit and thus provide less discomfort when worn by the wearer, and in which a sufficient heat generation period is likely to be obtained. In the case where the exothermic warmer 1 is configured to include an exothermic warmer main body and an outer jacket, the exothermic warmer main body has a thickness of preferably 10% or more and 80% or less, and more preferably 20% more and 60% or less of the thickness of the exothermic warmer 1. If the exothermic warmer main body has a thickness within the above-described ranges, and the outer jacket provided on the skin contact surface side of the first cover sheet 21 is made of a non-woven fabric, both a sufficient heat generation period and texture when worn are likely to be achieved. The thickness of the exothermic warmer 1 is measured using the following method.

Method for Measuring Thickness of Exothermic Warmer 1

An acrylic plate having a thickness of 3 mm is placed on a measurement site of the exothermic warmer 1, and the thickness of the measurement site is measured by using a non-contact laser displacement sensor (Laser Head LK-G30, Displacement Sensor LK-GD500) available from Keyence Corporation. The pressure applied to the exothermic warmer 1 to perform thickness measurement is set to 0.5 g/cm$^2$.

The exothermic warmer 1 according to the embodiment shown in FIG. 1 is preferably manufactured using the following method. First, an exothermic element forming step of forming an exothermic element is performed that includes: a step A of adding an electrolyte in a solid state to one surface of a second substrate sheet 13; and a step B of applying a coating material that contains an oxidizable metal, a carbon component, and water, but not the electrolyte. The step of adding an electrolyte in a solid state can be performed by means of spraying the electrolyte. The step of applying a coating material that contains an oxidizable metal, a carbon component, and water can be performed by applying the coating material by using, for example, an application apparatus such as a die coater. The order in which the step A and the step B are performed can be arbitrarily determined, and the step A and the step B may be performed in either order. It is also possible to simultaneously perform the step A and the step B.

After an exothermic element 11 has been formed through the process described above, or before the exothermic element 11 is formed, or between the two steps, namely, the step A and the step B of the exothermic element forming step, or concurrently with the formation of the exothermic element 11, a water-retaining material supplying step of supplying a water-retaining material 12 to an exothermic element 11 forming surface side of the second substrate sheet 13 on which the exothermic element 11 is formed (or is to be formed) is performed. The water-retaining material 12 can be supplied by means of spraying the water-retaining material 12. As a specific procedure, for example, the step of applying the coating material onto one surface of the second substrate sheet 13 is performed, then, the step of adding the electrolyte in a solid state is performed, and thereafter the step of supplying the water-retaining material is performed.

Then, a second cover sheet 22 is disposed on a non-exothermic element 11 forming surface side of the second substrate sheet 13, and also a first cover sheet 21 is disposed on the exothermic element 11 forming surface side of the second substrate sheet 13, and then extension portions 21a and 22a of the cover sheets 21 and 22 extending from the outer edges of the second substrate sheet 13 are joined to each other. In this way, an intended exothermic warmer 1 is obtained.

In the case of manufacturing the exothermic warmer 1 according to the embodiment shown in FIG. 7, after the exothermic element forming step and the water-retaining material supplying step described above, a first substrate sheet 14, which is a sheet separate from the second substrate sheet 13, is disposed on the exothermic element 11 forming surface side of the second substrate sheet 13. The first substrate sheet 14 may be a sheet that is the same as or different from the second substrate sheet 13. Due to the exothermic element 11 being interposed between the first substrate sheet 14 and the second substrate sheet 13, ease of handling of the sheet is improved, which leads to ease of manufacturing. Then, a step of covering the outer surface of the second substrate sheet 13 and the outer surface of the first substrate sheet 14 with a second cover sheet 22 and a first cover sheet 21 that serve as an outer wrapping sheet is performed. After this, the same process as that of the embodiment shown in FIG. 1 is performed.

Figure 8:
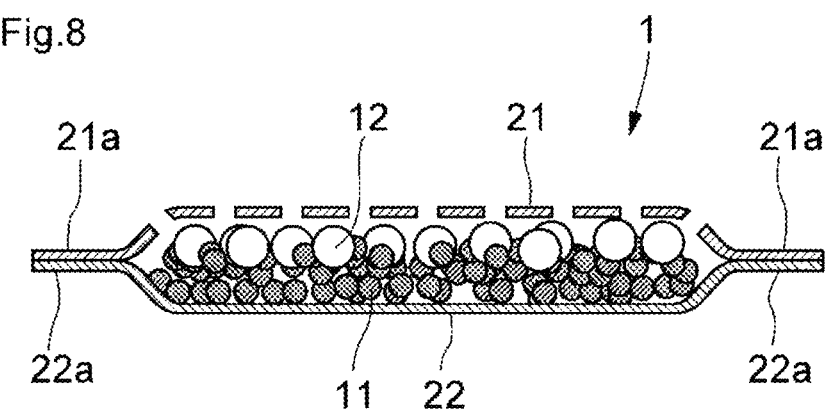
FIG. 8 is a cross-sectional view schematically showing an exothermic warmer according to a third embodiment of the present invention (a diagram that is equivalent to FIG. 1).

FIG. 8 shows an exothermic warmer 1 according to another embodiment of the present invention. The exothermic warmer 1 according to the present embodiment shown in the diagram is the same as the exothermic warmer 1 according to the embodiment shown in FIG. 1, except that the second substrate sheet 13 is not provided. In the present embodiment, the exothermic element 11 is formed directly on the second cover sheet 22, and the layer made of the water-retaining material 12 is formed directly on the exothermic element 11.

In the case of manufacturing the exothermic warmer 1 according to the present embodiment, first, an exothermic element forming step of forming an exothermic element is performed by performing a step of adding an electrolyte in a solid state to one surface of a second cover sheet 22 and a step of applying a coating material that contains an oxidizable metal, a carbon component, and water, but not the electrolyte, in this order or in a reversed order, or performing the two steps simultaneously. Then, after the exothermic element 11 has been formed through the above-described step, or between the two steps of the exothermic element forming step, or before the exothermic element 11 is formed, a water-retaining material supplying step of supplying a water-retaining material 12 to an exothermic element 11 forming surface side of the second cover sheet 22 on which the exothermic element 11 is formed (or is to be formed) is performed. After this, a first cover sheet 21 is disposed on the exothermic element 11 forming surface side of the second cover sheet 22, and then extension portions 21a and 22a of the cover sheets 21 and 22 extending from the outer edges of the second substrate sheet 13 are joined to each other. In this way, an intended exothermic warmer 1 is obtained.

An exothermic warmer 1 according to an embodiment shown in FIG. 9 is the same as that of the embodiment shown in FIG. 8, except that the exothermic element 11 and the water-retaining material 12 are in a mixed state. In this mixed state, at least a part of the water-retaining material 12 is in direct contact with the exothermic element 11. The exothermic warmer 1 according to the present embodiment can be obtained by performing, for example, a step of applying a coating material as described above onto one surface of the second substrate sheet 13, followed by a step of supplying a water-retaining material and a step of adding an electrolyte in a solid state.

In the case where the exothermic warmer 1 according to the present embodiment is manufactured using a different method, first, an exothermic element forming step of forming an exothermic element is performed by performing a step of adding an electrolyte in a solid state to one surface of a second cover sheet 22 and a step of applying a coating material that contains an oxidizable metal, a carbon component, and water, but not the electrolyte, in this order or in a reversed order, or performing the two steps simultaneously. Then, concurrently with the formation of the exothermic element 11, a water-retaining material supplying step of supplying a water-retaining material 12 to a surface side of the second cover sheet 22 on which the exothermic element 11 is to be formed is performed. Through this, the exothermic element 11 and the water-retaining material 12 are brought into a mixed state. After that, a first cover sheet 21 is disposed on the exothermic element 11 forming surface side of the second cover sheet 22, and then extension portions 21a and 22a of the cover sheets 21 and 22 extending from the outer edges of the second substrate sheet 13 are joined to each other. In this way, an intended exothermic warmer 1 is obtained.

The exothermic warmer 1 according to each of the embodiments given above is suitable for use to warm a human body. In this case, the exothermic warmer 1 may be used, with the first cover sheet 21 opposing the human body or with the second cover sheet 22 opposing the human body. From the viewpoint of efficiently warming a human body by using a large amount of steam generated from the exothermic warmer 1, it is preferable to use the exothermic warmer 1, with the first cover sheet 21 opposing the human body. In this case, it is preferable to bring the first cover sheet 21 into direct contact with the human body from the viewpoint of efficiently warming the human body, but an additional member may be interposed between the first cover sheet 21 and the human body.

Up to here, the present invention has been described by way of preferred embodiments thereof, but the present invention is not limited to the embodiments given above. For example, in the embodiments shown in FIGS. 1 and 8, the layer made of the water-retaining material 12 is disposed on a surface of the exothermic element 11 that is on the first cover sheet 21 side, but instead, the layer made of the water-retaining material 12 may be disposed on a surface of the exothermic element 11 that is on the second cover sheet 22 side.

In the embodiments shown in FIGS. 8 and 9, the exothermic element 11 is formed by applying the coating material onto the second cover sheet 22 so as to be flat, but instead, the exothermic element 11 may be formed by applying the coating material onto the first cover sheet 21 so as to be flat.

A portion omitted from the description of one of the embodiments given above and the requirements of one of the embodiments given above can be applied to the other embodiments as appropriate. Furthermore, the requirements of the embodiments can be replaced with each other as appropriate.

With respect to the embodiment described above, the present invention further discloses the exothermic warmer and the method for manufacturing an exothermic warmer described below.

<1> An exothermic warmer comprising:

an exothermic warmer main body that generates heat through an oxidation reaction and in which a flat-shaped exothermic element containing an oxidizable metal, an electrolyte, a carbon component, and water is covered with a first cover sheet and a second cover sheet, wherein the first cover sheet is a sheet that is air permeable and does not substantially limit the oxidation reaction, a water-retaining material is provided so as to be at least partially in contact with the exothermic element, and the exothermic warmer satisfies conditions (A) to (C) given below:

(A) a difference between an internal temperature of the exothermic element and a highest surface temperature of the exothermic warmer main body is 10° C. or less;

(B) a highest skin temperature obtained when the exothermic warmer is applied to human skin is 38° C. or more and 42° C. or less; and (C) a ratio of an amount (mg/cm$^2$·10 min) of steam generated in 10 minutes after the oxidation reaction has started to a mass (g/cm$^2$) of the exothermic element takes a value of 50 or more and 250 or less.

<2> The exothermic warmer as set forth in clause <1>, wherein, in a state before the oxidation reaction has started, the exothermic element has a water content of 9 mass % or more and 25 mass % or less.

<3> The exothermic warmer as set forth in clause <1> or <2>, wherein the water-retaining material is disposed on a surface of the exothermic element that is on the first cover sheet side or a surface of the exothermic element that is on the second cover sheet side.

<4> The exothermic warmer as set forth in any one of clauses <1> to <3>, wherein the exothermic element is formed by being applied in a flat shape on the first cover sheet or the second cover sheet.

<5> The exothermic warmer as set forth in any one of clauses <1> to <4>, wherein the exothermic element is formed on a substrate sheet, and the water-retaining material is disposed on a surface of the exothermic element that is opposite to a surface of the exothermic element that opposes the substrate sheet.

<6> The exothermic warmer as set forth in clause <5>, wherein an air permeable sheet is provided on the far side of the water-retaining material relative to the exothermic element.

<7> The exothermic warmer as set forth in any one of clauses <1> to <6>, wherein the water-retaining material is a water-absorbing polymer.

<8> The exothermic warmer as set forth in any one of clauses <1> to <7>, wherein the first cover sheet has an air permeability of 0 sec/(100 ml·6.42 cm$^2$) or more and 1500 sec/(100 ml·6.42 cm$^2$) or less, and a water pressure resistance of 1500 mmH$_2$O or more.

<9> The exothermic warmer as set forth in any one of clauses <1> to <8>, wherein, in a state before the oxidation reaction has started, the exothermic element has an electrolyte concentration of 1 mass % or more.

<10> The exothermic warmer as set forth in any one of clauses <1> to <8>, wherein, in a state before the oxidation reaction has started, the exothermic element has an electrolyte concentration of 20 mass % or less.

<11> The exothermic warmer as set forth in any one of clauses <1> to <10>, wherein, in a state before the oxidation reaction has started, the exothermic element has an electrolyte concentration of 3 mass % or more and 15 mass % or less.

<12> The exothermic warmer as set forth in any one of clauses <1> to <11>, wherein, in the state before the oxidation reaction has started, the exothermic element has an electrolyte concentration of 5 mass % or more and 10 mass % or less.

<13> The exothermic warmer as set forth in any one of clauses <1> to <12>, wherein, in a state before the oxidation reaction, a concentration of the electrolyte with respect to a total of an electrolyte amount and a water amount in the exothermic element is 5 mass % or more and 50 mass % or less.

<14> The exothermic warmer as set forth in any one of clauses <1> to <13>, wherein, in the state before the oxidation reaction, the concentration of the electrolyte with respect to the total of the electrolyte amount and the water amount in the exothermic element is 10 mass % or more and 40 mass % or less.

<15> The exothermic warmer as set forth in clause <7>, wherein the water-absorbing polymer is capable of retaining pure water in an amount that is 20 times or more its own weight.

<16> The exothermic warmer as set forth in any one of clauses <7> or <15>, wherein the water-absorbing polymer is capable of retaining water in an amount that is 3 times or more its own weight at 20° C., with respect to an aqueous solution having the same electrolyte concentration as a concentration of the electrolyte contained in the exothermic element in a state before the oxidation reaction has started.

<17> The exothermic warmer as set forth in clause <7>, <15> or <16>, wherein, in a state before the oxidation reaction has started, the water-absorbing polymer has a total water retention capacity, in terms of mass, of 1 time or more and 15 times or less of an amount of water contained in the exothermic element.

<18> The exothermic warmer as set forth in clause <7>, <15>, <16> or <17>, wherein, in the state before the oxidation reaction has started, the water-absorbing polymer has a total water retention capacity, in terms of mass, of 2 times or more and 10 times or less of the amount of water contained in the exothermic element.

<19> The exothermic warmer as set forth in any one of clauses <1> to <18>, wherein the exothermic warmer has a thickness of 0.5 mm or more and 8 mm or less.

<20> The exothermic warmer as set forth in clause <19>,
wherein the exothermic warmer has a thickness of 1 mm or more and 6 mm or less.
<21> The exothermic warmer as set forth in any one of any one of <1> to <20>,
wherein an outer jacket is provided on an outer side of the first cover sheet and/or the second cover sheet of the exothermic warmer main body.
<22> The exothermic warmer as set forth in clause <21>,
wherein the first cover sheet is located on a skin contact side that comes into contact with the skin of a wearer relative to the second cover sheet, and the outer jacket is provided on the skin contact side relative to the first cover sheet.
<23> The exothermic warmer as set forth in clause <21> or <22>,
wherein the outer jacket is a non-woven fabric.
<24> The exothermic warmer as set forth in any one of clauses <21> to <23>,
wherein a thickness of the exothermic warmer main body excluding the outer jacket in the exothermic warmer is 10% or more and 80% or less of a thickness of the exothermic warmer.
<25> The exothermic warmer as set forth in clause <24>,
wherein the thickness of the exothermic warmer main body excluding the outer jacket in the exothermic warmer is 20% or more and 60% or less of the thickness of the exothermic warmer.
<26> An exothermic warmer comprising:
an exothermic element that contains an oxidizable metal, an electrolyte, a carbon component, and water, and generates heat through an oxidation reaction; and
a water-absorbing polymer that is at least partially in contact with the exothermic element,
the exothermic element and the water-absorbing polymer being interposed between a first cover sheet that is air permeable and does not suppress the oxidation reaction and a second cover sheet,
wherein, in a state before the oxidation reaction has started, the exothermic element has a water content of 9 mass % or more and 25 mass % or less, and a concentration of the electrolyte of 1 mass % or more.
<27> The exothermic warmer as set forth in clause <26>,
wherein the water-absorbing polymer is capable of retaining water in an amount that is 3 times or more its own weight at 20° C., with respect to an aqueous solution having the same electrolyte concentration as the concentration of the electrolyte contained in the exothermic element in the state before the oxidation reaction has started.
<28> The exothermic warmer as set forth in clause <26> or <27>,
wherein an electrolyte content in the exothermic element before the oxidation reaction has started is 3 mass % or more.
<29> The exothermic warmer as set forth in any one of clauses <26> to <28>,
wherein the electrolyte content in the exothermic element before the oxidation reaction has started is 4 mass % or more.
<30> The exothermic warmer as set forth in any one of clauses <26> to <29>,
Wherein, in the state before the oxidation reaction has started, the water-absorbing polymer has a total water retention capacity, in terms of mass, of 1 time or more and 15 times or less of an amount of water contained in the exothermic element.

<31> The exothermic warmer as set forth in any one of clauses <26> to <30>,
wherein, in the state before the oxidation reaction has started, the water-absorbing polymer has a total water retention capacity, in terms of mass, of 2 times or more and 10 times or less of the amount of water contained in the exothermic element.
<32> The exothermic warmer as set forth in any one of clauses <26> to <31>,
wherein the exothermic element is formed by being applied in a flat shape on the first cover sheet or the second cover sheet.
<33> The exothermic warmer as set forth in any one of clauses <26> to <32>,
wherein the exothermic element is formed on a substrate sheet, and the water-retaining material is disposed on a surface of the exothermic element that is opposite to a surface of the exothermic element that opposes the substrate sheet.
<34> The exothermic warmer as set forth in any one of clauses <26> to <33>,
wherein an air permeable sheet is provided between the water-absorbing polymer and the first cover sheet.
<35> The exothermic warmer as set forth in any one of clauses <26> to <34>,
wherein the first cover sheet has an air permeability of 0 sec/(100 ml·6.42 $cm^2$) or more and 1500 sec/(100 ml·6.42 $cm^2$) or less, and a water pressure resistance of 1500 $mmH_2O$ or more.
<36> The exothermic warmer as set forth in any one of clauses <26> to <35>,
wherein the water-absorbing polymer is disposed on a surface of the exothermic element that is on the first cover sheet side.
<37> The exothermic warmer as set forth in any one of clauses <26> to <36>,
wherein the exothermic warmer has a thickness of 0.5 mm or more and 8 mm or less.
<38> The exothermic warmer as set forth in clause <37>,
wherein the exothermic warmer has a thickness of 1 mm or more and 6 mm or less.
<39> The exothermic warmer as set forth in any one of clauses <26> to <38>,
wherein. in the exothermic warmer, an outer jacket is provided on an outer side of the first cover sheet and/or the second cover sheet.
<40> The exothermic warmer as set forth in clause <39>,
wherein the first cover sheet is located on a skin contact side that comes into contact with the skin of a wearer relative to the second cover sheet, and the outer jacket is provided on the skin contact side relative to the first cover sheet.
<41> The exothermic warmer as set forth in clause <39> or <40>,
wherein the outer jacket is a non-woven fabric.
<42> The exothermic warmer as set forth in any one of clauses <39> to <41>,
wherein a thickness of the exothermic warmer main body excluding the outer jacket in the exothermic warmer is 10% or more and 80% or less of a thickness of the exothermic warmer.
<43> The exothermic warmer as set forth in clause <42>,
wherein the thickness of the exothermic warmer main body excluding the outer jacket in the exothermic warmer is 20% or more and 60% or less of the thickness of the exothermic warmer.
<44> A method for manufacturing an exothermic warmer in which an exothermic element containing an oxidizable metal, an electrolyte, a carbon component, and water is provided on a sheet, the method comprising:

an exothermic element forming step of forming an exothermic element that is performed by performing a step of adding the electrolyte in a solid state to one surface of the sheet and a step of applying a coating material that contains the oxidizable metal, the carbon component, and the water, but not the electrolyte, in this order or in a reversed order, or performing the two steps simultaneously, and before or after the exothermic element forming step, or between the two steps of the exothermic element forming step, or concurrently with the exothermic element forming step, a water-retaining material supplying step of supplying a water-retaining material to an exothermic element forming surface side of the sheet on which the exothermic element is formed, wherein an amount of water in the exothermic element is 9 mass % or more and 25 mass % or less.

<45> The method for manufacturing an exothermic warmer as set forth in clause <44>, wherein the step of applying the coating material onto one surface of the sheet is performed, thereafter, the step of supplying the water-retaining material is performed, and thereafter the step of adding the electrolyte in a solid state is performed.

<46> The method for manufacturing an exothermic warmer as set forth in clause <44> or <45>, wherein the step of applying the coating material onto one surface of the sheet is performed, thereafter, the step of adding the electrolyte in a solid state is performed, and thereafter the step of supplying the water-retaining material is performed.

<47> The method for manufacturing an exothermic warmer as set forth in any one of <44> to <46>, further comprising after the water-retaining material supplying step, a step of overlaying another sheet that is the same as or different from the sheet on the exothermic element forming surface side.

<48> The method for manufacturing an exothermic warmer as set forth in clause <46>, further comprising a step of covering each outer surface of the sheet and the other sheet with a sheet that serves as a cover sheet.

EXAMPLES

Hereinafter, the present invention will be described in further detail by way of examples. However, the scope of the present invention is not limited to the examples. Unless otherwise stated, the units "%" and "part" respectively mean "mass %" and "part by mass".

Examples 1 to 5, and Comparative Examples 1 and 2

An exothermic composition having the composition shown in Table 1 given below was prepared in the following procedure. A thickener was dissolved in water, and then table salt was dissolved therein to prepare an aqueous solution. Iron powder was introduced into the aqueous solution and stirred. Furthermore, activated carbon was introduced into the solution and stirred thoroughly until uniformly dispersed. An exothermic composition slurry was thereby obtained. In Examples 1 to 5, and Comparative Example 2, exothermic compositions having the same composition were used, and the air permeability of the first cover sheet was changed. The exothermic composition was applied to thin paper in which polyethylene was laminated (hereinafter also referred to as "PE laminate thin paper", with a basis weight of 31 g/m$^2$) with a basis weight of 700 g/m$^2$, and an exothermic element was thereby formed. Next, water-absorbing polymer particles, with a basis weight of 20 g/m$^2$, were sprayed onto the exothermic element to form a layer, and a water-retaining material layer was thereby formed. Crepe paper (with a basis weight of 65 g/m$^2$) was stacked onto the water-retaining material layer. A stacked exothermic element thus obtained was cut to a size of 50 mm×50 mm. Next, the stacked exothermic element was sandwiched by first and second cover sheets that had been cut to a size of 63 mm×63 mm, and four corners of the cover sheets were heat sealed. An exothermic warmer was thereby obtained. In Examples 2 to 5, and Comparative Example 2, as the first cover sheet, a moisture permeable sheet made of a microporous film obtained by biaxially drawing a polyethylene film containing calcium carbonate as a filler was used and disposed on the crepe paper side. As the second cover sheet, an air impermeable sheet (hereinafter also referred to as "PE laminate paper") in which polyethylene was laminated on paper was used and disposed on the PE laminate thin paper side. In Example 1, and Comparative Examples 1 to 3, as the first cover sheet, a spunbond non-woven fabric was used and disposed on the crepe paper side. The air permeability and the moisture permeability of the first cover sheet in each of the examples and comparative examples are as shown in Table 2. The first cover sheet (a spunbond non-woven fabric made of polypropylene and having a basis weight of 13 g/m$^2$) used in Example 1 had a water pressure resistance of 87 mmH$_2$O, and the first cover sheets used in Examples 2 to 5 all had a water pressure resistance exceeding 3000 mmH$_2$O.

TABLE 1

| Constituent element | Material/composition |
| --- | --- |
| First cover sheet | See Table 2 |
| First substrate sheet | Crepe paper with a basis weight of 65 g/m$^2$ |
| Water-retaining material | Water-absorbing polymer 40 mg/cell (with a basis weight of 20 g/m$^2$) |
| Exothermic composition | Applied amount: 1.68 g<br>Iron powder: 55.15%<br>Activated carbon: 4.39%<br>Water: 33.98%<br>Thickener: 0.14%<br>Phosphoric acid 3K: 0.98%<br>Common salt: 5.10%<br>48% KOH: 0.26% |
| Second substrate sheet | PE laminate thin paper with a basis weight of 31 g/cm$^2$ |
| Second cover sheet | PE laminate paper |

The following shows details of the materials constituting an exothermic warmer.

Iron: iron powder RKH2 available from Dowa IP Creation Co., Ltd.

Activated carbon: Carboraffin available from Japan Enviro Chemicals, Ltd.

Thickener (xanthan gum): ECHO GUM BT available from DSP Gokyo Food & Chemical, Co., Ltd.

Water: tap water

Table salt: pharmacopoeia sodium chloride available from Otsuka Chemical Co., Ltd.

Phosphoric acid 3K: tripotassium phosphate available from Yoneyama Chemical Industry, Co., Ltd.

48% KOH: 48% potassium hydroxide solution available from Kanto Chemical, Co., Inc.

Water-absorbing polymer: AQUALIC CAW-151, available from Nippon Shokubai, Co., Ltd.

PE laminate thin paper: MEGC21 available from Nittoku, Co., Ltd.

Crepe paper: white crepe paper available from Daishowa Paper Products, Inc.

PE laminate paper: KIPE71 available from Inogami KK

Moisture permeable sheet: TSF series available from Kohjin Film & Chemicals, Co., Ltd.

After an exothermic warmer has been manufactured, the exothermic warmer was placed and sealed in a pillow bag made of an aluminum deposited film so as to prevent an oxidation reaction from proceeding. In this state, the exothermic warmer was left for 24 hours, and then the exothermic warmer was taken out of the pillow bag in a nitrogen purged environment, and disassembled so as to measure the water content in the exothermic element. As a result, the water content in the exothermic element (Example 1) was 13%. In Examples 1 and 2, and Comparative Example 2, the water content was the same. In Example 3, the water content was 14.5%, and in Examples 4 and 5, the water content was 14.1%. In Comparative Example 1, the water content was 7.5%, and in Comparative Example 3, the water content was 8.0%. For the measurement of the water content, the amount of water emitted when the exothermic warmer was heated and dried at 100° C. for 30 minutes was measured by using a compact moisture meter (HB43 available from Mettler Toledo, Inc.), and the water content in the exothermic element was obtained.

In the exothermic warmers of Examples 1 to 5, the highest internal temperature of the exothermic element and the highest surface temperature of the exothermic warmer were measured. The internal temperature of the exothermic element was measured by inserting a K-type thermocouple into the inside of the crepe paper. The surface temperature of the exothermic warmer main body was measured by bringing a thermocouple into contact with the outer surface of the moisture permeable sheet. As a result, the difference between the highest temperatures was 6° C.

Next, the skin temperature when the exothermic warmer was applied to human skin was measured. The surfaces of a stacked exothermic element manufactured through the above-described process were sandwiched between an air-through non-woven fabric (made of PET/PE fibers and having a basis weight of 30 g/m$^2$) and a needle-punched non-woven fabric (made of PP/PE fibers and having a basis weight of 80 g/m$^2$), and the peripheral edge portions of the non-woven fabrics were bonded together with a hot melt adhesive, and an eye mask-shaped exothermic warmer was obtained. The air-through non-woven fabric was disposed on the crepe paper side. The needle-punched non-woven fabric was disposed on the PE laminate thin paper side. The air-through non-woven fabric side of the obtained exothermic warmer was applied to the eyes of a subject, and a thermocouple was attached to the upper eyelid of the subject so as to measure the skin surface temperature.

Skin surface temperature profiles in Examples 1 to 5 and Comparative Example 2 are shown in FIG. 6, and the highest temperatures obtained at this time are shown in Table 2. In Examples 1 to 5, substantially the same temperature profiles were observed, and the highest temperatures were 39.9° C. to 40.9° C. Also, a comfortable warmth was obtained during use. On the other hand, in the exothermic element of Comparative Example 2 in which a moisture permeable sheet having an air permeability of 2500 sec/(100 ml·6.42 cm$^2$) was used, the temperature profile delayed, and the highest temperature was 36.4° C. In Comparative Example 2, a sufficient warmth was not obtained during use.

TABLE 2

| | First cover sheet | | | | Proportion of water in exothermic element [%] | Difference between highest internal temperature of exothermic element and highest surface temperature of exothermic warmer main body [° C.] | Highest skin temperature [° C.] | Amount of steam/mass of exothermic element [(mg/cm$^2$ · 10 min)/ (g/cm$^2$)] |
|---|---|---|---|---|---|---|---|---|
| | Material | Air permeability [sec/ (100 ml · 6.42 cm$^2$)] | Moisture permeability [g/(m$^2$ · 24 h)] | Water pressure resistance [mmH$_2$O] | | | | |
| Example 1 | Spunbond non-woven fabric | 0 | 6767 | 87 | 13.0 | 6.0 | 39.9 | 94 |
| Example 2 | Moisture permeable sheet | 350 | 5282 | Over 3000 | 13.0 | 6.0 | 40.9 | 84 |
| Example 3 | Moisture permeable sheet | 500 | 4295 | Over 3000 | 14.5 | 6.0 | 40.3 | 84 |
| Example 4 | Moisture permeable sheet | 1000 | 2873 | Over 3000 | 14.1 | 6.0 | 40.3 | 65 |
| Example 5 | Moisture permeable sheet | 1500 | 2271 | Over 3000 | 14.1 | 6.0 | 40.9 | 53 |
| Comp. Ex. 1 | Spunbond non-woven fabric | 0 | 6767 | 87 | 7.5 | — | 43.7 | — |
| Comp. Ex. 2 | Moisture permeable sheet | 2500 | 1689 | Over 3000 | 13.0 | — | 36.4 | 38 |
| Comp. Ex. 3 | Needle-punched non-woven fabric | 0.1 | 6362 | 87 | 8.0 | — | 44.8 | — |

In the exothermic warmer of Comparative Example 1, the exothermic composition had the same composition as that of the exothermic compositions of Examples 1 to 5 and Comparative Example 2. In the manufacturing of the exothermic warmer of Comparative Example 1, an exothermic element was obtained by applying the exothermic composition onto a PE laminate thin paper (with a basis weight of 31 g/m²). As the water-retaining material 12, a polymer sheet (available from Inogami KK) was stacked on the exothermic element. The polymer sheet was a sheet in which a sheet of wood pulp paper (20 g/m²), a water-absorbing polymer (70 g/m², AQUALICCAW-151), and a sheet of wood pulp paper (30 g/m²) were stacked in this order to form a single sheet. As the moisture permeable sheet, the same moisture permeable sheet as that used in Example 1 was used. The exothermic element had the same configuration as that of Example 1, except for the water-retaining material 12. In the exothermic warmer obtained in Comparative Example 1, the exothermic element was not in direct contact with the water-absorbing polymer serving as the water-retaining material.

An eye mask-shaped exothermic warmer as that used in the skin surface temperature measurement described above was manufactured by using the stacked exothermic element obtained in Comparative Example 1. The skin surface temperature was measured by using the exothermic warmer, and the highest temperature was 43.7° C., which is the level at which it is unlikely to be safe for long-hour use. The reason is presumably that a sufficient amount of water was not supplied from the water-absorbing polymer to the exothermic element during the oxidation reaction.

Comparative Example 3

Example 1 disclosed in JP 2007-319359A was replicated. An exothermic warmer was manufactured by using the same materials as those disclosed in JP 2007-319359A as possible because not all of the same materials as disclosed therein were available. The configuration of the exothermic element was as shown in Table 3. A viscous exothermic composition was obtained by mixing iron powders, activated carbon, table salt, and carboxymethyl cellulose (hereinafter also referred to as "CMC"), thereafter adding water thereto, and kneading the mixture. Then, in order to manufacture an exothermic element, the viscous exothermic composition was applied, in a rectangular shape, onto a non-woven fabric (a needle-punched non-woven fabric with a basis weight of 80 g/m² and a water pressure resistance of 88 mmH₂O) serving as a substrate, which was leveled by using a 800 µm thick plate so as to stack the exothermic composition on the substrate. In this way, an exothermic element was formed. The obtained exothermic element weighed 5 g. On the exothermic element, a water-retaining material was sprayed in an amount of 5% of the viscous exothermic composition in terms of mass so as to stack the water-retaining material thereon, thereby forming a water-retaining material layer. Next, the water-retaining material layer was covered with an air impermeable covering material (laminate paper), which was bonded together, and the peripheral edge was cut. In this way, an exothermic warmer was manufactured. As the substrate 2 used in Example 1 of JP 2007-319359A, a non-woven fabric with an air permeability of 0.1 sec/(100 ml·6.42 cm²) was used.

Exothermic characteristics of the obtained exothermic warmer were evaluated using the following method. A thermocouple was attached to the skin of a subject, and the substrate 2 side of the obtained exothermic warmer was placed thereon. The skin surface temperature profile obtained at this time is shown in FIG. 10. The highest temperature is shown in Table 2. Measurement was performed three times, and variations were observed in the profile. The temperature reached 40° C. in about 3 minutes, and increased to the highest temperature of about 45° C. After 15 minutes of use, redness was observed on the skin. The cause is presumably that the initial amount of water was too low so that the temperature at the initial stage of the oxidation reaction was too high, and furthermore a sufficient amount of water was not supplied to the exothermic element during the oxidation reaction due to the relationship between the performance of the water-absorbing polymer and the salt concentration in the exothermic element, and thus it was not possible to suppress an increase in the temperature.

INDUSTRIAL APPLICABILITY

As described in detail above, according to the present invention, it is possible to provide a thin exothermic warmer with a good fit and in which the amount of steam generated per unit mass of the exothermic element is increased as compared to that of a conventional product on the market. Also, according to the present invention, it is possible to provide an exothermic warmer that uniformly warms the entire target area, with less skin temperature variations. Furthermore, according to the present invention, it is possible to provide an exothermic warmer that can control the skin temperature of the target area, is safe for use on the human body, and can provide a comfortable sense of warmth.

The invention claimed is:
1. An exothermic warmer comprising:
an exothermic warmer main body that generates heat through an oxidation reaction and in which a flat-shaped exothermic element comprising an oxidizable metal, an electrolyte, a carbon component, and water is covered with a first cover sheet and a second cover sheet,
wherein the first cover sheet is a sheet that is air permeable and does not substantially limit the oxidation reaction,
a water-retaining material is provided so as to be at least partially in contact with the exothermic element, and
the exothermic warmer satisfies conditions (A) to (C) given below:
(A) a difference between an internal temperature of the exothermic element and a highest surface temperature of the exothermic warmer main body is 10° C. or less;

TABLE 3

| Exothermic composition | Iron powder | 100 parts | RKH2 available from Dowa IP Creation Co., Ltd. |
|---|---|---|---|
| | Activated carbon | 2 parts | SA-PLUS available from Japan Norit |
| | Common salt | 3 parts | |
| | CMC | 0.4 parts | SEROGEN F-6HS9 available from DKS, Co., Ltd. |
| | Water | 40 parts | |
| Water-retaining material | | 5% of exothermic composition | SANFRESH ST-500D available from Sanyo Chemical Industries, Ltd. |
| Coating material | | | Laminate paper KIPE 71 |
| Non-woven fabric | | | Needle-punched non-woven fabric MLV |

(B) a highest skin temperature obtained when the exothermic warmer is applied to human skin is 38° C. to 42° C.; and (C) a ratio of an amount (mg/cm$^2$·10 min) of steam generated in 10 minutes after the oxidation reaction has started to a mass (g/cm$^2$) of the exothermic element takes a value of 50 to 250, wherein, in a state before the oxidation reaction has started, the exothermic element has a water content of 9 mass % to 25 mass %.

2. The exothermic warmer according to claim 1, wherein the water-retaining material is disposed on a surface of the exothermic element that is on the first cover sheet side or a surface of the exothermic element that is on the second cover sheet side.

3. The exothermic warmer according to claim 1, wherein the exothermic element is formed on a substrate sheet, and the water-retaining material is disposed on a surface of the exothermic element that is opposite to a surface of the exothermic element that opposes the substrate sheet.

4. The exothermic warmer according to claim 3, wherein an air permeable sheet is provided on the far side of the water-retaining material relative to the exothermic element.

5. The exothermic warmer according to claim 1, wherein the water-retaining material is a water-absorbing polymer.

6. The exothermic warmer according to claim 1, wherein the first cover sheet has an air permeability of 0 sec/(100 ml·6.42 cm$^2$) to 1500 sec/(100 ml·6.42 cm$^2$), and a water pressure resistance of 1500 mmH$_2$O or more.

7. The exothermic warmer according to claim 1, wherein, in a state before the oxidation reaction has started, the exothermic element has an electrolyte concentration of 1 mass % or more.

8. The exothermic warmer according to claim 1, wherein, in a state before the oxidation reaction has started, the exothermic element has an electrolyte concentration of 20 mass % or less.

9. The exothermic warmer according to claim 1, wherein, in a state before the oxidation reaction has started, the exothermic element has an electrolyte concentration of 3 mass % to 15 mass %.

10. The exothermic warmer according to claim 9, wherein, in the state before the oxidation reaction has started, the exothermic element has an electrolyte concentration of 5 mass % to 10 mass %.

11. The exothermic warmer according to claim 1, wherein, in a state before the oxidation reaction, a concentration of the electrolyte with respect to a total of an electrolyte amount and a water amount in the exothermic element is 5 mass % to 50 mass %.

12. The exothermic warmer according to claim 11, wherein, in the state before the oxidation reaction, the concentration of the electrolyte with respect to the total of the electrolyte amount and the water amount in the exothermic element is 10 mass % to 40 mass %.

13. The exothermic warmer according to claim 5, wherein the water-absorbing polymer is capable of retaining pure water in an amount that is 20 times or more its own weight.

14. The exothermic warmer according to claim 5, wherein the water-absorbing polymer is capable of retaining water in an amount that is 3 times or more its own weight at 20° C., with respect to an aqueous solution having the same electrolyte concentration as a concentration of the electrolyte contained in the exothermic element in a state before the oxidation reaction has started.

15. The exothermic warmer according to claim 5, wherein, in a state before the oxidation reaction has started, the water-absorbing polymer has a total water retention capacity, in terms of mass, of 1 to 15 times of an amount of water contained in the exothermic element.

16. The exothermic warmer according to claim 15, wherein, in the state before the oxidation reaction has started, the water-absorbing polymer has a total water retention capacity, in terms of mass, of 2 to 10 times the amount of water contained in the exothermic element.

17. The exothermic warmer according to claim 1, wherein the exothermic warmer has a thickness of 0.5 mm to 8 mm.

18. The exothermic warmer according to claim 17, wherein the exothermic warmer has a thickness of 1 mm to 6 mm.

19. The exothermic warmer according to claim 1, wherein an outer jacket is provided on an outer side of the first cover sheet and/or the second cover sheet of the exothermic warmer main body.

20. The exothermic warmer according to claim 19, wherein the first cover sheet is located on a skin contact side that comes into contact with the skin of a wearer relative to the second cover sheet, and the outer jacket is provided on the skin contact side relative to the first cover sheet.

21. The exothermic warmer according to claim 19, wherein the outer jacket is a non-woven fabric.

22. The exothermic warmer according to claim 19, wherein a thickness of the exothermic warmer main body excluding the outer jacket in the exothermic warmer is 10% to 80% of a thickness of the exothermic warmer.

23. The exothermic warmer according to claim 22, wherein the thickness of the exothermic warmer main body excluding the outer jacket in the exothermic warmer is 20% to 60% of the thickness of the exothermic warmer.

24. An exothermic warmer comprising:

an exothermic element that comprises an oxidizable metal, an electrolyte, a carbon component, and water, and generates heat through an oxidation reaction; and a water-absorbing polymer that is at least partially in contact with the exothermic element, the exothermic element and the water-absorbing polymer being interposed between a first cover sheet that is air permeable and does not suppress the oxidation reaction and a second cover sheet, wherein, in a state before the oxidation reaction has started, the exothermic element has a water content of 9 mass % to 25 mass %, and a concentration of the electrolyte of 1 mass % or more, wherein the water-absorbing polymer is capable of retaining water in an amount that is 3 times or more its own weight at 20° C., with respect to an aqueous solution having the same electrolyte concentration as the concentration of the electrolyte contained in the exothermic element in the state before the oxidation reaction has started.

25. The exothermic warmer according to claim 24, wherein an electrolyte content in the exothermic element before the oxidation reaction has started is 3 mass % or more.

26. The exothermic warmer according to claim 25, wherein the electrolyte content in the exothermic element before the oxidation reaction has started is 4 mass % or more.

27. The exothermic warmer according to claim 24, wherein, in the state before the oxidation reaction has started, the water-absorbing polymer has a total water retention capacity, in terms of mass, of 1 to 15 times of an amount of water contained in the exothermic element.

28. The exothermic warmer according to claim 27, wherein, in the state before the oxidation reaction has started, the water-absorbing polymer has a total water retention capacity, in terms of mass, of 2 to 10 times of the amount of water contained in the exothermic element.

29. The exothermic warmer according to claim 24, wherein the exothermic element is formed by being applied in a flat shape on the first cover sheet or the second cover sheet.

30. The exothermic warmer according to claim 24, wherein the exothermic element is formed on a substrate sheet, and the water-retaining material is disposed on a surface of the exothermic element that is opposite to a surface of the exothermic element that opposes the substrate sheet.

31. The exothermic warmer according to claim 24, wherein an air permeable sheet is provided between the water-absorbing polymer and the first cover sheet.

32. The exothermic warmer according to claim 24, wherein the first cover sheet has an air permeability of 0 sec/(100 ml·6.42 cm$^2$) to 1500 sec/(100 ml·6.42 cm$^2$), and a water pressure resistance of 1500 mmH$_2$O or more.

33. The exothermic warmer according to claim 24, wherein the water-absorbing polymer is disposed on a surface of the exothermic element that is on the first cover sheet side.

34. The exothermic warmer according to claim 24, wherein the exothermic warmer has a thickness of 0.5 mm to 8 mm.

35. The exothermic warmer according to claim 34, wherein the exothermic warmer has a thickness of 1 mm to 6 mm.

36. The exothermic warmer according to claim 24, wherein, in the exothermic warmer, an outer jacket is provided on an outer side of the first cover sheet and/or the second cover sheet.

37. The exothermic warmer according to claim 36, wherein the first cover sheet is located on a skin contact side that comes into contact with the skin of a wearer relative to the second cover sheet, and the outer jacket is provided on the skin contact side relative to the first cover sheet.

38. The exothermic warmer according to claim 36, wherein the outer jacket is a non-woven fabric.

39. The exothermic warmer according to claim 36, wherein a thickness of the exothermic warmer main body excluding the outer jacket in the exothermic warmer is 10% to 80% of a thickness of the exothermic warmer.

40. The exothermic warmer according to claim 39, wherein the thickness of the exothermic warmer main body excluding the outer jacket in the exothermic warmer is 20% to 60% of the thickness of the exothermic warmer.

41. A method for manufacturing an exothermic warmer in which an exothermic element comprising an oxidizable metal, an electrolyte, a carbon component, and water is provided on a sheet, the method comprising:
forming an exothermic element by adding the electrolyte in a solid state to one surface of the sheet and applying a coating material that comprises the oxidizable metal, the carbon component, and the water, but not the electrolyte, in this order or in a reversed order, or performing the two steps simultaneously,
before or after the exothermic element forming step, or between the two steps of the exothermic element forming step, or concurrently with the exothermic element forming step, supplying a water-retaining material to an exothermic element forming surface side of the sheet on which the exothermic element is formed, and
after the water-retaining material supplying step, overlaying another sheet that is the same as or different from the sheet on the exothermic element forming surface side,
wherein an amount of water in the exothermic element is 9 mass % or more and 25 mass % or less.

42. The method for manufacturing an exothermic warmer according to claim 41,
wherein the applying the coating material onto one surface of the sheet is performed, thereafter, supplying the water-retaining material is performed, and thereafter the adding the electrolyte in a solid state is performed.

43. The method for manufacturing an exothermic warmer according to claim 41,
wherein the applying the coating material onto one surface of the sheet is performed, thereafter, the adding the electrolyte in a solid state is performed, and thereafter the supplying the water-retaining material is performed.

44. The method for manufacturing an exothermic warmer according to claim 43, further comprising
covering each outer surface of the sheet and the other sheet with a sheet that serves as a cover sheet.

* * * * *